(12) United States Patent
Foot et al.

(10) Patent No.: US 10,982,210 B2
(45) Date of Patent: Apr. 20, 2021

(54) COMPOSITIONS FOR DELIVERY OF CARGO TO CELLS

(71) Applicant: Sixfold Bioscience Ltd., London (GB)

(72) Inventors: George Foot, Dorchester (GB); Anna Perdrix Rosell, Lleida (ES); Zuzanna Brzosko, Wolka Pracka (PL)

(73) Assignee: Sixfold Bioscience Ltd., London (GB)

( * ) Notice: Subject to any disclaimer, the term of this patent is extended or adjusted under 35 U.S.C. 154(b) by 0 days.

(21) Appl. No.: 16/290,348

(22) Filed: Mar. 1, 2019

(65) Prior Publication Data

US 2019/0270991 A1    Sep. 5, 2019

Related U.S. Application Data

(60) Provisional application No. 62/721,891, filed on Aug. 23, 2018, provisional application No. 62/638,586, filed on Mar. 5, 2018, provisional application No. 62/637,705, filed on Mar. 2, 2018.

(51) Int. Cl.
| | |
|---|---|
| *A61K 31/7088* | (2006.01) |
| *C12N 15/113* | (2010.01) |
| *A61K 35/17* | (2015.01) |
| *C07K 16/28* | (2006.01) |
| *C12N 5/0783* | (2010.01) |
| *C12N 15/87* | (2006.01) |
| *C12N 15/115* | (2010.01) |
| *C12N 15/11* | (2006.01) |
| *B82Y 5/00* | (2011.01) |

(52) U.S. Cl.
CPC ........ *C12N 15/113* (2013.01); *A61K 31/7088* (2013.01); *A61K 35/17* (2013.01); *C07K 16/2818* (2013.01); *C12N 5/0636* (2013.01); *C12N 5/0646* (2013.01); *C12N 15/11* (2013.01); *C12N 15/115* (2013.01); *C12N 15/87* (2013.01); *B82Y 5/00* (2013.01); *C12N 2310/16* (2013.01); *C12N 2310/315* (2013.01); *C12N 2310/321* (2013.01); *C12N 2310/322* (2013.01); *C12N 2310/3231* (2013.01); *C12N 2310/3233* (2013.01)

(58) Field of Classification Search
None
See application file for complete search history.

(56) References Cited

U.S. PATENT DOCUMENTS

| 4,166,452 | A | 9/1979 | Generales, Jr. |
|---|---|---|---|
| 4,256,108 | A | 3/1981 | Theeuwes |
| 4,265,874 | A | 5/1981 | Bonsen et al. |
| 6,214,841 | B1 | 4/2001 | Jackson et al. |
| 7,655,787 | B2 | 2/2010 | Guo et al. |
| 7,842,793 | B2 | 11/2010 | Rothemund |
| 8,058,069 | B2 | 11/2011 | Yaworski et al. |
| 8,088,912 | B2 | 1/2012 | Guo et al. |
| 8,163,291 | B2 | 4/2012 | Chang et al. |
| 8,883,994 | B2 | 11/2014 | Wang et al. |
| 8,916,696 | B2 | 12/2014 | Rossi et al. |
| 8,932,593 | B2 | 1/2015 | Chang et al. |
| 9,176,122 | B2 | 11/2015 | Burnette |
| 9,228,207 | B2 | 1/2016 | Liu et al. |
| 9,297,013 | B2 | 3/2016 | Guo |
| 9,388,418 | B2 | 7/2016 | Rossi et al. |
| 9,732,337 | B2 | 8/2017 | Shapiro et al. |
| 10,300,148 | B2 | 5/2019 | Lee et al. |
| 10,301,621 | B2 * | 5/2019 | Shapiro ................. C12N 15/111 |
| 2003/0232877 | A1 | 12/2003 | Sikorski et al. |
| 2005/0260651 | A1 | 11/2005 | Callas et al. |
| 2006/0228300 | A1 | 10/2006 | Chang et al. |
| 2006/0228357 | A1 | 10/2006 | Chang et al. |
| 2009/0004644 | A1 | 1/2009 | Kiel et al. |
| 2009/0191225 | A1 | 7/2009 | Chang et al. |
| 2010/0003753 | A1 | 1/2010 | Guo |
| 2010/0016409 | A1 | 1/2010 | Yingling et al. |
| 2010/0240732 | A1 | 9/2010 | Gilboa |
| 2011/0008251 | A1 | 1/2011 | Chang et al. |
| 2011/0143417 | A1 | 6/2011 | Chang et al. |
| 2012/0196346 | A1 | 8/2012 | Chang et al. |
| 2012/0263648 | A1 | 10/2012 | Shapiro et al. |
| 2013/0022538 | A1 | 1/2013 | Rossi et al. |
| 2013/0209514 | A1 | 8/2013 | Gilboa et al. |
| 2014/0179758 | A1 | 6/2014 | Guo |
| 2014/0221253 | A1 | 8/2014 | Johnston et al. |
| 2015/0086584 | A1 | 3/2015 | Gilboa et al. |
| 2015/0166998 | A1 | 6/2015 | Rossi et al. |
| 2015/0232883 | A1 | 8/2015 | Dahlman et al. |

(Continued)

FOREIGN PATENT DOCUMENTS

| WO | 2002016596 A2 | 2/2002 |
|---|---|---|
| WO | 2005003293 A2 | 1/2005 |

(Continued)

OTHER PUBLICATIONS

Li, 2015, RNA as a stable polymer to build controllable and defined nanostructures for material and biomedical applications, Nano Today. 10(5):631-655.
Li, 2016, Controllable Self-assembly of RNA Tetrahedrons with Precise Shape and Size for Cancer Targeting, Adv Mater. 28(34):7501-7507.
Liu, 2015, Cancer targeted therapeutics: From molecules to drug delivery vehicles, J Control Release. 219:632-643.
Lonn, 2016, Enhancing Endosomal Escape for Intracellular Delivery of Macromolecular Biologic Therapeutics, Sci Rep. 6:32301.
Ma, 2014, Enhancing endosomal escape for nanoparticle mediated siRNA delivery, Nanoscale. 6(12):6415-25.

(Continued)

*Primary Examiner* — Michael D Burkhart
(74) *Attorney, Agent, or Firm* — Brown Rudnick LLP; Adam M. Schoen

(57) ABSTRACT

The invention provides compositions for delivery of cargo to cells. The invention also provides compositions that bind multiple agents simultaneously. The compositions are useful as therapeutics. Methods of using the compositions are also provided.

19 Claims, 11 Drawing Sheets

Specification includes a Sequence Listing.

(56) References Cited

U.S. PATENT DOCUMENTS

| | | | |
|---|---|---|---|
| 2015/0359907 | A1 | 12/2015 | Getts et al. |
| 2016/0032292 | A1 | 2/2016 | Storici et al. |
| 2016/0051693 | A1 | 2/2016 | Getts et al. |
| 2016/0145348 | A1* | 5/2016 | Stephan ............... A61K 38/177 424/450 |
| 2016/0237142 | A1 | 6/2016 | Olichon et al. |
| 2016/0208245 | A1 | 7/2016 | Ahn et al. |
| 2017/0079916 | A1 | 3/2017 | Khan et al. |
| 2017/0121708 | A1 | 5/2017 | Shapiro et al. |
| 2017/0175122 | A1 | 6/2017 | Guo et al. |
| 2017/0209599 | A1 | 7/2017 | Getts et al. |
| 2017/0306335 | A1 | 10/2017 | Zhang et al. |
| 2017/0312299 | A1 | 11/2017 | Getts et al. |
| 2017/0349894 | A1 | 12/2017 | Dahlman et al. |
| 2018/0028686 | A1 | 2/2018 | Brinker et al. |
| 2018/0185417 | A1 | 7/2018 | Joly et al. |

FOREIGN PATENT DOCUMENTS

| | | |
|---|---|---|
| WO | 2005110489 A2 | 11/2005 |
| WO | 2006107617 A2 | 10/2006 |
| WO | 2006107786 A2 | 10/2006 |
| WO | 2007016507 A2 | 2/2007 |
| WO | 2008039254 A9 | 8/2008 |
| WO | 2009046104 A1 | 4/2009 |
| WO | 2010017544 A2 | 2/2010 |
| WO | 2010144295 A1 | 12/2010 |
| WO | 2010148085 A1 | 12/2010 |
| WO | 2012094586 A2 | 7/2012 |
| WO | 2012170372 A2 | 12/2012 |
| WO | 2013075132 A1 | 5/2013 |
| WO | 2013075140 A1 | 5/2013 |
| WO | 2013142255 A2 | 9/2013 |
| WO | 2014039809 A2 | 3/2014 |
| WO | 2014121050 A1 | 8/2014 |
| WO | 2014153394 A1 | 9/2014 |
| WO | 2015042101 A1 | 3/2015 |
| WO | 2015171827 A1 | 11/2015 |
| WO | 2015196146 A2 | 12/2015 |
| WO | 2016124765 A1 | 8/2016 |
| WO | 2016144755 A1 | 9/2016 |
| WO | 2016145003 A1 | 9/2016 |
| WO | 2016145005 A1 | 9/2016 |
| WO | 2016168784 A2 | 10/2016 |
| WO | 2016201129 A1 | 12/2016 |
| WO | 201 7147557 A1 | 8/2017 |
| WO | 2017139758 A1 | 8/2017 |
| WO | 2017143150 A1 | 8/2017 |
| WO | 2017143156 A1 | 8/2017 |
| WO | 2017143171 A1 | 8/2017 |
| WO | 2017176894 A1 | 10/2017 |
| WO | 2017197009 A1 | 11/2017 |
| WO | 2018118587 A1 | 6/2018 |

OTHER PUBLICATIONS

Maier, 2012, Acid-labile traceless click linker for protein transduction, J Am Chem Soc. 134(24); 10169-10173.
Makarova, 2011, Evolution and classification of the CRISPR-Cas systems, Nat. Rev. Microbiol. 9:467-477.
Miersch, 2012, Synthetic antibodies: concepts, potential and practical considerations, Methods. 57(4):486-98.
Milton, 2015, Nuclease resistant oligonucleotides with cell penetrating properties, Chem Commun (Camb). 51(19):4044-47.
Misak, 2014, Albumin-based nanocomposite spheres for advanced drug delivery systems, Biotechnol J. 9(1):163-70.
Morsut, 2016, Engineering customized cell sensing and response behaviors using synthetic notch receptors, Cell. 164:780-91.
Moss, 2019, Lipid Nanoparticles for Delivery of Therapeutic RNA Oligonucleotides, Mol. Pharmaceutics. 16(6):2265-2277.
Nair, 2014, Multivalent N-Acetylgalactosamine-Conjugated siRNA Localizes in Hepatocytes and Elicits Robust RNAi-Mediated Gene Silencing, J. Am. Chem. Soc., 136(49):6958-16961.
Oh, 2018, Cloaking nanoparticles with protein corona shield for targeted drug delivery, Nat Commun. 9(1):4548.
Oishi, 2005, Lactosylated poly(ethylene glycol)-siRNA conjugate through acid-labile beta-thiopropionate linkage to aonstruct pH-sensitive polyion complex micelles achieving enhanced gene silencing in hepatoma cells, J Am Chem Soc. 127(6):1624-1625.
Okada, 2011, Novel complementary peptides to target molecules, Anticancer Res. 31(7):2511-6.
O'Keefe, 2013, siRNAs and shRNAs: Tools for Protein Knockdown by Gene Silencing, Mater Methods. 3:197.
Paredes, 2011, RNA labeling, conjugation and ligation, Methods. 54(2); 251-259.
Pramod, 2015, Real-Time Drug Release Analysis of Enzyme and pH Responsive Polysaccharide Nanovesicles, J Phys Chem B. 119(33):10511-10523.
Prhavc, 2003,2'-O-[2-[2-(N,N-dimethylamino)ethoxy]ethyl] modified oligonucleotides: symbiosis of charge interaction factors and stereoelectronic effects, Org Lett. 5(12):2017-20.
Recchia, 2006, Retroviral vector integration deregulates gene expression but has no consequence on the biology and function of transplanted T cells. Proc. Natl. Acad. Sci. U.S.A. 103(5):1457-1462.
Rose, 2017, Rapidly inducible Cas9 and DSB-ddPCR to probe editing kinetics, Nat. Methods. 14:891-896.
Samanta, 2016, Nanoparticles and DNA—a powerful and growing functional combination in bionanotechnology, Nanoscale. 8(17):9037-9095.
Santos-Cancel, 2017, Collagen Membranes with Ribonuclease Inhibitors for Long-Term Stability of Electrochemical Aptamer-Based Sensors Employing RNA, Anal Chem. 89(10):5598-5604.
Senel, 2019, Applications of Lipidic and Polymeric Nanoparticles for siRNA Delivery, Intech Open. (16 pages).
Shen, 2016, Screening of efficient polymers for siRNA delivery in a library of hydrophobically modified polyethyleneimines, Journal of Materials Chemistry B. 4(39):6468-6474.
Shin, 2018, Recent Advances in RNA Therapeutics and RNA Delivery Systems Based on Nanoparticles, Adv. Therap. 1(7):1800065.
Shu, 2013, Fabrication of pRNA nanoparticles to deliver therapeutic RNAs and bioactive compounds into tumor cells, Nat Protoc. 8(9):1635-59.
Shu, 2011, Assembly of Multifunctional Phi29 pRNA Nanoparticles for Specific Delivery of SiRNA and other Therapeutics to Targeted Cells, Methods. 54(2):204-214.
Shum, 2013, Nucleic Acid Aptamers as Potential Therapeutic and Diagnostic Agents for Lymphoma, J Cancer Ther. 4(4):872-890.
Singh, 2019, CRISPR/Cas9 guided genome and epigenome engineering and its therapeutic applications in immune mediated diseases, Semin Cell Dev Biol. S1084-9521(18):30111-3.
Smith, 2016, Chimeric antigen receptor (CAR) T cell therapy for malignant cancers:Summary and perspective, J. Cellular Immnother. 2(2):59-68.
Sorek, 2013, CRISPR Mediated Adaptive Immune Systems in Bacteria and Archaea, Ann. Rev. Biochem. 82:237-266.
Sparvath, 2017, Computer-Aided Design of RNA Origami Structures. In:Ke Y., Wang R (eds) 3D DNA Nanostructure. Methods in Molecular Biology. vol. 1500.
Straathof, 2005, An inducible caspase 9 safety switch for T-cell therapy, Blood. 105(11):4247-4254.
Sun, 2016, Factors influencing the nuclear targeting ability of nuclear localization signals, J Drug Target. 24(10):927-933.
Van Der Oost, 2014, CRISPR-based adaptive and heritable immunity in prokaryotes, Trends in Biochemical Sciences. 34(8):401-407.
Van Loenen, 2013, Multicistronic vector encoding optimized safety switch for adoptive therapy with T-cell receptormodified T cells, Gene Ther 20(8):861-7.
Wang, 2013. RNA-DNA hybrid origami:folding of a long RNA single strand into complex nanostructures using short DNA helper strands, Chem Commun (Camb). 49(48):5462-4.
Wu, 2017, A Fusion Receptor as a Safety Switch, Detection, and Purification Biomarker for Adoptive Transferred T Cells, Mol Ther. 25(10):2270-2279.

(56) References Cited

OTHER PUBLICATIONS

Xu, 2018, Favorable Biodistribution, Specific Targeting and Conditional Endosomal Escape of RNA Nanoparticles in Cancer Therapy, Cancer Lett. 414:57-70.
Ye, 2018, Engineering chimeric antigen receptor-T cells for cancer treatment, Mol. Cancer. 17(1):32.
Zhou, 2015, Cell-Specific RNA Aptamer against Human CCR5 Specifically Targets HIV-1 Susceptible Cells and Inhibits HIV-1 Infectivity, Chemistry & Biology 22(3):379-390.
Zumrut, 2016, Ligand-guided selection of aptamers against T-cell Receptorcluster of differentiation 3 (TCR-CD3) expressed on Jurkat. E6 cells, Anal Biochem. 512:1-7.
Alomari, 2015, Personalised dosing: Printing a dose of ones own medicine, Int J Pharm. 494(2):568-577.
Afonin, 2012, Co-transcriptional Assembly of Chemically Modified RNA Nanoparticles Functionalized with siRNAs, Nano Lett. 12(10):5192-5195.
Afonin, 2011, Design and self-assembly of siRNA-functionalized RNA nanoparticies for use in automated nanomedicine, Nat Protoc. 6(12):2022-2034.
Afonin, 2014, Multifunctional RNA Nanoparticles, Nano Lett. 14(10):5662-71.
Andrukh, 2011, Wire-in-a-nozzle as a new droplet-on-demand electrogenerator, Langmuir. 27(6):3206-10.
Arumugam, 2011, Enterotypes of the human gut microbiome, Nature. 473(7346):174-180.
Binzel, 2016, Specific Delivery of MiRNA for High Efficient Inhibition of Prostate Cancer by RNA Nanotechnology, Mol Ther. 24(7):1267-77.
Cao, 2016, An easy and efficient inducible CRISPR/Cas9 platform with improved specificity for multiple gene targeting, Nucleic Acids Res. 14(19):e149.
Chan, 2017, Exploiting the Protein Corona from Cell Lysate on DNA Functionalized Gold Nanoparticles for Enhanced mRNA Translation, ACS Appl. Mater. Interfaces, 9:10408-10417.
Chen 2018, A compound chimeric antigen receptor strategy for targeting multiple myeloma, Leukemia. 32:402-412.
Chworos, 2004, Building Programmable Jigsaw Puzzles with RNA, Science. 306(5704):2068-72.
Ciceri, 2009, Infusion of suicide gene-engineered donor lymphocytes after family haploidentical haemopoietic stem-cell transplantation for leukaemia (the TK007 trial): a non-randomised phase I-II study, Lancet Oncol. 10:489-500.
Deglane, 2006, Impact of the guanidinium group on hybridization and cellular uptake of cationic oligonucleotides, Chembiochem, 7(4):684-92.
Dominguez, 2016, Beyond editing: repurposing CRISPR—Cas9 for precision genome regulation and interrogation, Nat. Rev. Cell Biol. 17(1):5-15.
Douglas, 2012, A Logic-Gated Nanorobot for Targeted Transport of Molecular Payloads, Science. 335(6070):831-4.
Elzoghby, 2012, Albumin-based nanoparticies as potential controlled release drug delivery systems, J Control Release. 157(2):168-82.
Endo, 2014, Preparation of chemically modified RNA origami nanostructures, Chemistry. 20(47):15330-3.
Fan, 2008, Development of a drop-on-demand droplet generator for one-drop-fill technology, Sensors and Actuators A, Physical. 147(2,3):649-655.
Fan, 2015, Bispecific antibodies and their applications, Journal of Hematology & Oncology. 8:130.
Gargett, 2014, The inducible caspase-9 suicide gene system as a "safety switch" to limit on-target, off-tumor toxicities of chimeric antigen receptor T cells, Front. Pharmacol. 5:235.
Garrett; 2011; Archaeal CRISPR-based immune systems: exchangeable functional modules; Trends in Microbiol. 19(11):549-556.
Geary, 2014, A single-stranded architecture for cotranscriptional folding of RNA nanostructures, Science. 345 (6198):799-804.
Geary, 2011, Promoting RNA helical stacking via A-minor junctions, Nucleic Acids Res. 39(3):1066-1080.
Gilleron, 2013, Image-based analysis of lipid nanoparticle-mediated siRNA delivery, intracellular trafficking and endosomal escape, Nat Biotechnol. 31(7):638-46.
Gujrati, 2016, Multifunctional pH-Sensitive Amino Lipids for siRNA Delivery, Bioconjug Chem. 27(1):19-35.
Guo, Nanoparticles Escaping RES and Endosome: Challenges for siRNA Delivery for Cancer Therapy, J. Nanomaterials. 2011(742895) (12 pages).
Guo, 2017, Size, Shape, and Sequence-Dependent Immunogenicity of RNA Nanoparticles, Mol Ther Nucleic Acids. (9):399-408.
Halman, 2017, Functionally-interdependent shape-switching nanoparticles with controllable properties, Nucleic Acids Research. 45(4):2210-2220.
Han, 2017, Single-stranded DNA and RNA origami, Science. 358(6369):2648.
Hoeprich, 2003, Bacterial virus phi29 pRNA as a hammerhead ribozyme escort to destroy hepatitis B virus, Gene Ther. 10:1258-1267.
Huang, 2016, Delivery of Therapeutics Targeting the mRNABinding Protein HuR Using 3DNA Nanocarriers Suppresses Ovarian Tumor Growth, Cancer Res, 76(6):1549-59.
Humphreys, 2019, Plasma and Liver Protein Binding of N-Acetylgalactosamine-Conjugated Small Interfering RNA, Drug Metab Dispos. 47(10):1174-1182.
Icten, 2015, Dropwise additive manufacturing of pharmaceutical products for melt-based dosage forms, J Pharm Sci. 104(5):1641-9.
International Search Report and Written Opinion dated Jul. 23, 2019, for International Patent Application PCT/IB2019/000209 with International filing date Mar. 1, 2019 (21 pages).
Jain, 2018, MicroRNAs Enable mRNA Therapeutics to Selectively Program Cancer Cells to Self-Destruct, Nucleic Acid Ther. 26(5):285-296.
Jakiela, 2014, Generation of Nanoliter Droplets on Demand at Hundred-Hz Frequencies; Micromachines, 5(4):1002-1011.
Janas, 2017, Impact of Oligonucleotide Structure, Chemistry, and Delivery Method on in Vitro Cytotoxicity, Nucleic Acid Ther. 27(1):11-22.
Jasinski, 2017, Advancement of the Emerging Field of RNA Nanotechnology, ACS Nano. 11(2):1142-1164.
Juliano, 2015, Cellular uptake and intracellular trafficking of oligonucleotides, Adv Drug Deliv Rev. 87:35-45.
Kariko, 2008, Incorporation of pseudouridine into mRNA yields superior nonimmunogenic vector with increased translational capacity and biological stability, Mol Ther. 16(11):1833-40.
Kariko, 2011, Generating the optimal mRNA for therapy: HPLC purification eliminates immune activation and improves translation of nucleoside-modified, protein-encoding mRNA, Nucleic Acids Res. 39(21):e142.
Kettler, 2014, Cellular uptake of nanoparticles as determined by particle properties, experimental conditions, and cell type, Environ Toxicol Chem. 33(3):481-92.
Khaled, 2005, Controllable Self-Assembly of Nanoparticles for Specific Delivery of Multiple Therapeutic Molecules to Cancer Cells Using RNA Nanotechnology, Nano Lett. 5(9):1797-1808.
Khaleghi, 2012, A caspase 8-based suicide switch induces apoptosis in nanobody-directed chimeric receptor expressing T cells, International journal of hematology. 95(4):434-44.
Kienast, 2013, Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy, Clin Cancer Res. 19(24):6730-40.
Kim, 2015, Self-assembled Messenger RNA Nanoparticles (mRNA-NPs) for Efficient Gene Expression, Sci Rep. 5:12737.
Klein, 2001, The kink-turn: a new RNA secondary structure motif, EMBO J. 20(15):4214-4221.
Knouse, 2018, Unlocking P(V): Reagents for chiral phosphorothioate synthesis, Science, 361(6408):1234-1238.
Krissanaprasit, 2019, Genetically Encoded, Functional Single-Strand RNA Origami: Anticoagulant, Adv Mater. 31 (21):e1808262.
Kurrikoff, 2016, Recent in vivo advances in cell-penetrating peptide-assisted drug delivery, Expert Opin Drug Deliv. 13(3):373-87.

(56) References Cited

OTHER PUBLICATIONS

Lee, 2015, RNA nanoparticle as a vector for targeted siRNA delivery into glioblastoma mouse model, Oncotarget. 6(17):14766-14776.

* cited by examiner

_US 10,982,210 B2_

SEQUENCE LISTING

```
<160> NUMBER OF SEQ ID NOS: 18

<210> SEQ ID NO 1
<211> LENGTH: 113
<212> TYPE: RNA
<213> ORGANISM: Artificial Sequence
<220> FEATURE:
<223> OTHER INFORMATION: synthetic

<400> SEQUENCE: 1
ggcaaccgca cagacucugu gaaggaggca cgcagagucu gugcccaaau caacaagagg      60
ugaagccugc acgccucuug uugaugguug ccauuuuuuu uuuuuuuuuu uuu            113

<210> SEQ ID NO 2
<211> LENGTH: 113
<212> TYPE: RNA
<213> ORGANISM: Artificial Sequence
<220> FEATURE:
<223> OTHER INFORMATION: Synthetic

<400> SEQUENCE: 2
ggcaaccgca cagacucugu gaagcgagca cgcagagucu gugcccaaau caacaagagg      60
ugaagccucc acgccucuug uugaugguug ccauuuuuuu uuuuuuuuuu uuu            113
```

<210> SEQ ID NO 3
<211> LENGTH: 113
<212> TYPE: RNA
<213> ORGANISM: Artificial Sequence
<220> FEATURE:
<223> OTHER INFORMATION: synthetic

<400> SEQUENCE: 3
ggcaaccgca cagacucugu gaagcaggca cgcagagucu gugcccaaau caacaagagg    60
ugaagcucgc acgccucuug uugaugguug ccauuuuuuu uuuuuuuuuu uuu           113

<210> SEQ ID NO 4
<211> LENGTH: 127
<212> TYPE: RNA
<213> ORGANISM: Artificial Sequence
<220> FEATURE:
<223> OTHER INFORMATION: synthetic

<400> SEQUENCE: 4
ggcaaccgca cagacucugu gaaggaggca cgcagagucu gugcccaaau caacaagagg    60
ugaagccugc acgccucuug uugaugguug ccgucgug gggcaucgag uaaaugcaau     120
ucgacac                                                              127

<210> SEQ ID NO 5
<211> LENGTH: 133
<212> TYPE: RNA
<213> ORGANISM: Artificial Sequence
<220> FEATURE:
<223> OTHER INFORMATION: synthetic

<400> SEQUENCE: 5
ggcaaccgca cagacucugu gaaggaggca cgcagagucu gugcccaaau caacaagagg    60
ugaagccugc acgccucuug uugaugguug ccggccuuag uaacgugcuu ugaugucgau   120
ucgacaggag gcc                                                       133

<210> SEQ ID NO 6
<211> LENGTH: 113
<212> TYPE: RNA
<213> ORGANISM: Artificial Sequence
<220> FEATURE:
<223> OTHER INFORMATION: synthetic
<220> FEATURE:
<221> NAME/KEY: n
<222> LOCATION: (1)..(113)
<223> OTHER INFORMATION: n = thymine
<220> FEATURE:
<221> NAME/KEY: misc_feature
<222> LOCATION: (1)..(113)
<223> OTHER INFORMATION: n = thymine

<400> SEQUENCE: 6
gggacggacg cgaaucuagu cuaaggaggc aagacuagau ucgcccugaa gaguagcgaa    60
guggacacgc nacncnncag guaacguucc ucauuuuuuu uuuuuuuuuu uuu           113

<210> SEQ ID NO 7
<211> LENGTH: 113
<212> TYPE: RNA
<213> ORGANISM: Artificial Sequence
<220> FEATURE:
<223> OTHER INFORMATION: synthetic
<220> FEATURE:
<221> NAME/KEY: n
<222> LOCATION: (1)..(113)

<223> OTHER INFORMATION: n = thymine
<220> FEATURE:
<221> NAME/KEY: misc_feature
<222> LOCATION: (1)..(113)
<223> OTHER INFORMATION: n = thymine

<400> SEQUENCE: 7
gggacggacg cgaaucuagu cuaaguccac aagacuagau ucgcccugaa gaguagcgaa    60
gccugcacgc nacncnncag guaacguucc ucauuuuuuu uuuuuuuuuu uuu          113

<210> SEQ ID NO 8
<211> LENGTH: 113
<212> TYPE: RNA
<213> ORGANISM: Artificial Sequence
<220> FEATURE:
<223> OTHER INFORMATION: synthetic
<220> FEATURE:
<221> NAME/KEY: n
<222> LOCATION: (1)..(113)
<223> OTHER INFORMATION: n = thymine
<220> FEATURE:
<221> NAME/KEY: misc_feature
<222> LOCATION: (1)..(113)
<223> OTHER INFORMATION: n = thymine

<400> SEQUENCE: 8
gggacggacg cgaaucuagu cuaagcaggc aagacuagau ucgcccugaa gaguagcgaa    60
gcgagcacgc nacncnncag guaacguucc ucauuuuuuu uuuuuuuuuu uuu          113

<210> SEQ ID NO 9
<211> LENGTH: 113
<212> TYPE: RNA
<213> ORGANISM: Artificial Sequence
<220> FEATURE:
<223> OTHER INFORMATION: Synthetic
<220> FEATURE:
<221> NAME/KEY: n
<222> LOCATION: (1)..(113)
<223> OTHER INFORMATION: n = thymine
<220> FEATURE:
<221> NAME/KEY: misc_feature
<222> LOCATION: (1)..(113)
<223> OTHER INFORMATION: n = thymine

<400> SEQUENCE: 9
gggacggacg cgaaucuagu cuaagcucgc aagacuagau ucgcccugaa gaguagcgaa    60
gccuccacgc nacncnncag guaacguucc ucauuuuuuu uuuuuuuuuu uuu          113

<210> SEQ ID NO 10
<211> LENGTH: 125
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(125)
<223> OTHER INFORMATION: n = thymine

<400> SEQUENCE: 10
gggacggacg cgaaucuagu cuaaggaggc aagacuagau ucgcccugaa gaguagcgaa    60
guggacacgc nacncnncag guaacguucc gugucguggg gcaucgagua aaugcaauuc   120
gacac                                                              125

<210> SEQ ID NO 11
<211> LENGTH: 131

```
<212> TYPE: RNA
<213> ORGANISM: Artificial Sequence
<220> FEATURE:
<223> OTHER INFORMATION: Synthetic
<220> FEATURE:
<221> NAME/KEY: n
<222> LOCATION: (1)..(131)
<223> OTHER INFORMATION: n = thymine
<220> FEATURE:
<221> NAME/KEY: misc_feature
<222> LOCATION: (71)..(71)
<223> OTHER INFORMATION: n is a, c, g, or u
<220> FEATURE:
<221> NAME/KEY: misc_feature
<222> LOCATION: (74)..(74)
<223> OTHER INFORMATION: n is a, c, g, or u
<220> FEATURE:
<221> NAME/KEY: misc_feature
<222> LOCATION: (76)..(77)
<223> OTHER INFORMATION: n is a, c, g, or u

<400> SEQUENCE: 11
gggacggacg cgaaucuagu cuaaggaggc aagacuagau ucgcccugaa gaguagcgaa      60
guggacacgc nacncnncag guaacguucc ggccuuagua acgugcuuug augucgauuc     120
gacaggaggc c                                                         131

<210> SEQ ID NO 12
<211> LENGTH: 66
<212> TYPE: RNA
<213> ORGANISM: Artificial Sequence
<220> FEATURE:
<223> OTHER INFORMATION: Synthetic

<400> SEQUENCE: 12
gggaacgguc cacucguucc cgucacuaga accauccuag ugaccauuuu uuuuuuuuu       60 uuuuuu                                                                66

<210> SEQ ID NO 13
<211> LENGTH: 66
<212> TYPE: RNA
<213> ORGANISM: Artificial Sequence
<220> FEATURE:
<223> OTHER INFORMATION: Synthetic

<400> SEQUENCE: 13
gggaacgggu gacucguucc cgucacuaga guggaccuag ugaccauuuu uuuuuuuuu       60 uuuuuu                                                                66

<210> SEQ ID NO 14
<211> LENGTH: 66
<212> TYPE: RNA
<213> ORGANISM: Artificial Sequence
<220> FEATURE:
<223> OTHER INFORMATION: Synthetic

<400> SEQUENCE: 14
gggaacgacc acgacguucc cgucacuaga gucacccuag ugaccauuuu uuuuuuuuu       60 uuuuuu                                                                66

<210> SEQ ID NO 15
<211> LENGTH: 66
<212> TYPE: RNA
<213> ORGANISM: Artificial Sequence
<220> FEATURE:
<223> OTHER INFORMATION: Synthetic
```

```
<400> SEQUENCE: 15
gggaacggcg aagucguucc cgucacuagu cguggucuag ugaccauuuu uuuuuuuuuu    60
uuuuuu                                                              66

<210> SEQ ID NO 16
<211> LENGTH: 66
<212> TYPE: RNA
<213> ORGANISM: Artificial Sequence
<220> FEATURE:
<223> OTHER INFORMATION: Synthetic

<400> SEQUENCE: 16
gggaacggag acgucguucc cgucacuaga cuucgccuag ugaccauuuu uuuuuuuuuu    60
uuuuuu                                                              66

<210> SEQ ID NO 17
<211> LENGTH: 66
<212> TYPE: RNA
<213> ORGANISM: Artificial Sequence
<220> FEATURE:
<223> OTHER INFORMATION: Synthetic

<400> SEQUENCE: 17
gggaacggau gguucguucc cgucacuaga cgucuccuag ugaccauuuu uuuuuuuuuu    60
uuuuuu                                                              66

<210> SEQ ID NO 18
<211> LENGTH: 81
<212> TYPE: RNA
<213> ORGANISM: Artificial Sequence
<220> FEATURE:
<223> OTHER INFORMATION: synthetic

<400> SEQUENCE: 18
gggaacgguc cacucguucc cgucacuaga accauccuag ugaccacugu cguggggcau    60
cgaguaaaug caauucgaca g                                             81
```

COMPOSITIONS FOR DELIVERY OF CARGO TO CELLS

CROSS-REFERENCE TO RELATED APPLICATIONS

This application claims the benefit of, and priority to, U.S. Provisional Patent Application No. 62/637,705, filed Mar. 2, 2018, U.S. Provisional Patent Application No. 62/638,586, filed Mar. 5, 2018, and U.S. Provisional Patent Application No. 62/721,891, the contents of each of which are incorporated herein by reference.

FIELD OF THE INVENTION

The invention relates generally to compositions and methods for delivery of cargo to cells.

SEQUENCE LISTING

This application contains a Sequence Listing, which has been submitted electronically in ASCII format and is hereby incorporated by reference in its entirety. The ASCII file, created on Feb. 28, 2019, is named SIX-001-03US-SeqList_ST25.txt and is 6 kilobytes in size.

BACKGROUND

Each year over 8 million people die worldwide from cancer or cancer-related illnesses. Cancer results from unchecked cell growth, and the unregulated cells invade other parts of the body, hijack nutritional resources, and impair the function of other tissues. Cancer is an indiscriminate killer: although lifestyle factors, such as smoking and diet, can increase one's risk of getting cancer, many cancers are attributable to a person's genetic makeup or to unknown causes. Nearly two in five people will be diagnosed with cancer at some point in their lives.

One strategy for cancer treatment is to use one or more agents that kill actively proliferating cells. For example, chemotherapeutics, such as doxorubicin and 5-fluorouracil, prevent cell division by blocking DNA replication but do not discriminate between cancerous and non-cancerous cells. Consequently, traditional chemotherapeutics kill cancer cells as well as normal cells in tissues where cell turnover is high, such as in the gastrointestinal tract and bone marrow, where blood cells are regenerated. As a result of this brute force approach, patients typically experience serious side effects.

More recently, cancer therapies have focused on the use of reagents that target molecules, such as proteins, involved in the growth or spread of cancer cells. However, targeted therapies have their own limitations. First, delivery of the reagent to its target within the body can be challenging. In addition, cancer cells can develop resistance to a targeted reagent. For example, the target can mutate, or the cancer cells can adapt to become independent of the pathway in which the target functions. Thus, the ability to deliver potent agents to cancer cells to prevent their growth is limited, and millions of people continue to die from cancer each year.

SUMMARY

The invention provides compositions for delivery of cargo to targeted cells, such as cancer cells, using a nanoparticle (e.g., nucleic acid (DNA and/or RNA) nanoparticle) linked to one or more cargoes, which may alter the function of the target cell. Numerous different cargoes and uses are discussed herein.

A particularly beneficial use for compositions of the invention is treating cancer. The invention recognizes that cancers are driven by multiple different genetic pathways, even within the same tumor (i.e. intra-tumor heterogeneity), meaning that more than one therapy is usually required to kill cancer cells efficiently. However, the vast majority of treatments both in the clinic and under development are designed to target one protein or cellular pathway. Selected cells can remain unaffected or adapt, thereby giving rise to therapy-resistant tumors (i.e. drug resistance). Compositions of the invention solve this problem by providing a single nanoparticle functionalized with different amounts of different cancer therapeutics or targeted delivery to cancer cells. In that manner, the invention provides targeted drug delivery systems capable of delivering drug compounds to targeted cells with minimal or no impact on other healthy cells, thereby limiting painful side-effects and increasing efficiency. Additionally, the drug delivery systems of the invention are able to carry and deliver more than one drug payload so that multiple cancer pathways can be blocked simultaneously to prevent drug resistance from developing.

Other uses of the compositions of the invention are also described, typically using different cargo linked to a nanoparticle. For example, the cargo may be a nucleic acid, peptide, or protein that affects gene expression in target cells. In certain embodiments, the cargo may be a component of the Clustered Regularly Interspaced Short Palindromic Repeats (CRISPR) system or a nucleic acid that promotes expression of a chimeric antigen receptor (CAR) or T cell receptor (TCR) in the target cell. Still other compositions include a nucleic acid nanoparticle linked to multiple binding moieties that can bring different cell types into proximity with each other or alter the activities of multiple pathways simultaneously. Other uses of the compositions include treatment of diseases other than cancer, such as infectious diseases or genetic disorders.

As discussed above, the compositions of the invention find a beneficial use in treating cancer and other diseases. As exemplified herein, the invention encompasses more than the use of different cancer drugs in different amounts on a single nanoparticle. Other aspects of the invention provide compositions that allow delivery of a cargo, such as a CRISPR component to afflicted cells. The CRISPR system permits sequence-specific gene editing within a cell, so the compositions of invention can be used to kill or repair cancer cells without affecting normal cells. In other embodiments, compositions for delivery of CARs or TCRs to immune cells, such as T cells, are provided. Those compositions allow the CAR-expressing or TCR-expressing cells to identify and destroy cancer cells or other diseased cells. Compositions with multivalent nanoparticles have a variety of therapeutic applications. For example, they can be used to draw T cells into contact with cancer cells or infected cells to facilitate T cell-mediated killing of the diseased cells. Alternatively, they can downregulate multiple cancer-promoting signaling pathways with a single multifunctionalized nanoparticle. In another application, such nanoparticles allow one to concomitantly deliver multiple therapeutic agents in different amounts to cancer cells. Specific examples are now described below.

In an aspect, the invention provides compositions containing a nucleic acid nanoparticle linked to two or more different moieties in different amounts. For example, the nanoparticle may be linked to one moiety in a first amount and to another moiety in a different amount. The first and second amount may differ by any quantifiable measure, such as number of molecules, mass, or size. The nanoparticle may be linked to a targeting moiety.

The moieties may be any type of moiety that exerts an effect on a cell. For example, each of the moieties may be a biologically active molecule, label, reporter, stabilizing agent, targeting moiety, or therapeutic agent. The different moieties may be of the same type, or they may be of different types. The moieties may be small molecule agents or biologic agents.

The moieties may be agents useful to treat cancer. The moieties may be chemotherapeutics. The moieties may be chemotherapeutics that are effective at different concentrations. The chemotherapeutics may be attached to the nanoparticle in different amounts so that they are provided at different concentrations. Preferably, each chemotherapeutic is provided at or near a concentration at which it is effective for treating cancer. Each of the moieties may independently be actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, or vinorelbine.

One or more of the moieties may be labels that facilitate identification of a cell. The label may be a fluorescent molecule, optical label, light-emitting molecule, phosphorescent molecule, dye, radiolabel, enzyme, or substrate.

In another aspect, the invention provides compositions containing a nucleic acid nanoparticle linked to a CRISPR component. The nanoparticle may be linked to multiple CRISPR components. The nanoparticle may be linked to one or more targeting moieties.

In other aspects, the invention provides compositions containing a nucleic acid nanoparticle linked to a nucleic acid that promotes expression of a CAR or TCR in an immune cell. The nanoparticle may be linked to multiple nucleic acid that promote expression of one or more chimeric antigen receptors. The nanoparticle may be linked to one or more targeting moieties.

In another aspect, the invention provides compositions containing a nucleic acid linked to a targeting moiety. The nucleic acid promotes expression of a chimeric antigen receptor in an immune cell, and the targeting moiety binds to a target on an immune cell.

In other aspects, the invention provides compositions containing a RNA nanoparticle linked to a nucleic acid that encodes a gene product that is expressed in a target cell. The RNA nanoparticle may be linked to multiple nucleic acids that encode one or more gene products that are expressed in a target cell. The RNA nanoparticle may be linked to one or more targeting moieties.

In another aspect, the invention provides compositions containing a nucleic acid nanoparticle linked to one binding moiety that binds to a target on one target cell and another binding moiety that binds to a different target on another target cell. Binding of the two binding moieties to their targets may cause the two target cells to associate with each other.

Preferably, the two target cells are different from each other. One of the target cells may be a an immune cell, such as a T cell, T regulatory ($T_{reg}$) cell, memory T cell, effector memory T cell, central memory T cell, naïve T cell, cytotoxic T cell, gamma delta T cell, B cell, natural killer (NK) cell, natural killer T (NKT) cell, megakaryocyte, platelet, erythroblast, erythrocyte, myeloblast, monoblast, monocyte, macrophage, dendritic cell, neutrophil, basophil, eosinophil, or precursor of any of the aforementioned cells. The other target cell may be a cancer cell or an infected cell. Binding of the targeting moieties to the targets may cause the T cell, NK cell, NKT cell, or macrophage to associate with cancer cell or infected cell and initiate an immune response against the cancer cell or infected cell. Association of the two cell types may lead to the destruction of the cancer cell or infected cell.

In another aspect, the invention provides compositions containing a nucleic acid nanoparticle linked to a binding moiety that binds to a target on a target cell and another binding moiety that binds to a different target on the same target cell. Binding of the first moiety to its target may alter the activity of a first pathway in the target cell, and binding of the second moiety to its target may alter the activity of a second pathway in the target cell.

In an aspect, the invention provides compositions containing a nucleic acid nanoparticle linked to two or more binding moieties that bind to different cell-free circulating effectors of a disorder. The nanoparticle may be linked to one or more targeting moieties.

In an aspect, the invention provides compositions containing a nanoparticle linked to one or more one CRISPR components linked and to one or more targeting moieties.

In embodiments of the invention that include a nucleic acid nanoparticle, the nucleic acid nanoparticle may be a RNA nanoparticle, a DNA nanoparticle, or a mixed RNA/DNA nanoparticle. The RNA nanoparticle may have an ordered structure. For example, the RNA nanoparticle may be a nanoarray, nanocage, nanocube, nanoprism, nanoring, nanoscaffold, or nanotube. The RNA nanoring may be made of 3, 4, 5, 6, 7, 8, or more individual RNA molecules. Each RNA molecule may contact two or more neighboring RNA molecules in the ring. The RNA nanoring may be symmetrical.

Nucleic acid nanoparticles of the invention may include one or more modified nucleotides, such a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholine, and phosphorothioate modification. Other modified nucleotides include 5caC, 5fC, 5hoC, 5hmC, 5meC/5fu, 5meC/5moU, 5meC/$^{th}$G, 5moC, 5meC/5camU, 5meC, ψ, 5meC/ψ, 5moC/5moU, 5moC/5meU, 5hmC/5meU, me1ψ, 5meC/me1ψ, 5moU, 5camU, m6A, 5hmC/ψ, 5moC/ψ, me6DAP, me4C, and 5fu.

Nucleic acid components of the nucleic nanoparticles may be folded using DNA or RNA origami techniques to enhance stability or cell entry.

In embodiments of the invention that include an agent, such as a moiety, binding moiety, effector, or receptor, that affects a pathway, the pathway may be a signaling, biochemical, metabolic, or genetic pathway. The pathway may be associated with a disease, such as cancer. The agent may alter the activity of a pathway. For example, each agent may increase or decrease activity of a pathway.

In embodiments of the invention that include multiple agents that affect pathways, the agents may target different pathways. The agents may alter the activity of their respective pathways at different concentrations. Preferably, each agent is attached to the nanoparticle so that it is provided at or near a concentration at which it alters the activity of a target pathway. The agents may alter one or more pathways in different cells, or they may alter one or more pathways in the same cell.

In embodiments of the invention that include a targeting moiety, the targeting moiety may be any moiety that facilitates delivery of the composition to a cell, compartment within a cell, or component of a cell. The targeting moiety may bind to a component on a cell or in a cell. For example, the targeting moiety may bind to a component on the surface of a cell or a component in an intracellular compartment of a cell. The targeting moiety may be an antibody, aptamer, ligand, nucleic acid, peptide, protein, receptor, carbohydrate, e.g., N-acetylgalactosamine, or any other molecule that facilitates binding of the nanoparticle to a cellular component. In other compositions, the targeting moiety is attached directly to a cargo, i.e., no nanoparticle is required.

In embodiments of the invention that include a CRISPR component, the CRISPR component may be RNA, DNA, protein, or a combination thereof, such as a ribonucleoprotein. The DNA may be closed-ended linear duplex (CELiD) DNA. The RNA may be a mRNA that encodes a CRISPR polypeptide. The mRNA may also encode a targeting peptide, such as a nuclear localization sequence. The mRNA may be complexed with antisense DNA. The RNA may be a guide RNA, e.g., a single guide RNA, or portion of a guide RNA, such as a crRNA, or tracrRNA. The CRISPR polypeptide may be an endonuclease or a helicase or a portion of an endonuclease or helicase. The CRISPR polypeptide may have endonuclease activity, helicase activity, or both. The CRISPR polypeptide may be catalytically active. The CRISPR polypeptide may function as a sequence-specific transcriptional activator or inhibitor, either by itself or in combination with another component.

The CRISPR component may alter expression of a target in a cell. For example, the CRISPR component may increase or decrease expression of a target in a cell.

In embodiments of the invention that include a nucleic acid that promotes expression of a chimeric antigen receptor, the nucleic acid may be DNA or RNA. The RNA may be mRNA, tracrRNA, crRNA, single guide RNA, miRNA, shRNA, or siRNA. The DNA may be closed-ended linear duplex (CELiD) DNA. The nucleic acid may encode a chimeric antigen receptor. The nucleic acid may promote expression of a chimeric antigen receptor or TCR by regulating expression of the receptor.

Therapeutic nucleic acids of the invention may contain one or more modified nucleotides, such a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholino, and phosphorothioate modification. Other modified nucleotides include 5caC, 5fC, 5hoC, 5hmC, 5meC/5fu, 5meC/5moU, 5meC/$^{th}$G, 5moC, 5meC/5camU, 5meC, Ψ, 5meC/ψ, 5moC/5moU, 5moC/5meU, 5hmC/5meU, me1ψ, 5meC/me1ψ, 5moU, 5camU, m6A, 5hmC/ψ, 5moC/ψ, me6DAP, me4C, and 5fu.

Therapeutic nucleic acids may be folded using DNA or RNA origami techniques to enhance stability or cell entry.

In embodiments of the invention that include compositions related to an immune cell, the immune cell may be any cell of the immune system, e.g., a cell of lymphoid or myeloid lineage. The immune cell may be a T cell, T regulatory ($T_{reg}$) cell, memory T cell, effector memory T cell, central memory T cell, naïve T cell, cytotoxic T cell, gamma delta T cell, B cell, natural killer (NK) cell, natural killer T (NKT) cell, megakaryocyte, platelet, erythroblast, erythrocyte, myeloblast, monoblast, monocyte, macrophage, dendritic cell, neutrophil, basophil, eosinophil, or precursor of any of the aforementioned cells. The immune cell may express one or more of CD3, CD4, CD8, CD25, and CD56.

In embodiments of the invention that include a nucleic acid that encodes a gene product, the nucleic acid may be a DNA or RNA. The DNA may be closed-ended linear duplex (CELiD) DNA. The RNA may be a mRNA. The mRNA may also encode a targeting peptide, such as a nuclear localization sequence. The mRNA may be complexed with antisense DNA. The gene product may be a RNA, polypeptide, or protein. The gene product may be a receptor that is expressed on the surface of a target cell. The receptor may be a chimeric antigen receptor.

In embodiments of the invention that include a binding moiety, the binding moiety may be any moiety that binds to a component of a cell, such as a protein, receptor, or surface molecule. The binding moiety may bind to a component on a cell or in a cell. For example, the binding moiety may bind to a component on the surface of a cell or a component in an intracellular compartment of a cell. The binding moiety may be an antibody, aptamer, ligand, nucleic acid, peptide, protein, receptor, or any other molecule that facilitates binding of the nanoparticle to a cellular component. The binding moieties may be of the same type, e.g., antibodies, aptamers, etc., or they may be of different types. Preferably, a binding moiety is an aptamer. The aptamer may contain one or more modified nucleotides, such a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholine, and phosphorothioate modification. Other modified nucleotides include 5caC, 5fC, 5hoC, 5hmC, 5meC/5fu, 5meC/5moU, 5meC/$^{th}$G, 5moC, 5meC/5camU, 5meC, ψ, 5meC/ψ, 5moC/5moU, 5moC/5meU, 5hmC/5meU, me1ψ, 5meC/me1ψ, 5moU, 5camU, m6A, 5hmC/ψ, 5moC/ψ, me6DAP, me4C, and 5fu.

Aptamers may be folded using DNA or RNA origami techniques to enhance stability or cell entry.

In embodiments of the invention that include compositions that bind to a target on a target cell, the target may be a molecule on or in a target cell. For example, a target may be a molecule expressed on the surface of the target cell, such as a receptor. Exemplary targets include 5T4, ALDH1, alpha V beta 6 integrin, ARMX3, AXL, B2MG, BCMA, C4.4A, CA6, CA9, Cadherin 6, CAIX, carcinoembryonic antigen (CEA), CCR1, CCR10, CCR4, CCR5, CCR6, CCR8, CD1d, CD3, CD4, CD5, CD8, CD9, CD11c, CD13, CD14, CD15, CD16, CD16A, CD19, CD20, CD22, CD25, CD27, CD28, CD30, CD31, CD32, CD32B, CD33, CD34, CD37, CD38, CD39, CD41, CD44, CD44v6, CD45R, CD45RA, CD45RO, CD47, CD49b, CD51, CD54, CD56, CD57, CD61, CD62, CD62E, CD62L, CD64, CD66b, CD69, CD70, CD74, CD79B, CD79 alpha/beta, CD80, CD81, CD83, CD86, CD94/NKG2, CD103, CD117, CD119, CD123, CD127, CD133, CD134, CD137, CD138, CD146, CD154, CD160, CD161/NK1.1, CD164, CD171, CD172a, CD180, CD194, CD197, CD202b, CD205, CD206, CD207, CD215, CD223, CD235a, CD252, CD268, CD269, CD272, CD273, CD282, CD284, CD307d, CD309, CD317, CD326, CD369, CD370, c-Kit, c-MET, Criptoprotein, Crth2, CTLA-R, CXCR3, CXCR4, CXCR5, DCIR2, DEP1, DLL3, EBP50, EDG-1/S1P1, EDNRB, EFNA4, EGFR, EGFRvIII, EMR1, ENPP3, epithelial cell adhesion molecule (EpCAM), EphA2, ErbB, ErbB2, FAP, Fas ligand, FGFR2, FGFR3, fibroblast activation protein (FAP), FLT3, folate receptor-alpha, GARP, GD2, GITR, glypican 3, gp100, gpA33, GPC3, GPNMB, GUCY2C, HGF, HER2, HER3, HLA-DR, IFN-gamma R, IgG, IGF-1R, IL-1R5, IL-1 RI, IL-6R, IL-6R alpha, IL-13 receptor α, IL-18R alpha, IL-21R, IL-23R, kappa light chain, KIR Family, L1 cell adhesion molecule (L1CAM), LAMP-1, LANCL1, LAP, Lewis Y, LFA-1, LIV-1, LRRC15, MAGE family members, mesothelin, MET, MHCII, MSLN, MUC1, MUC16, NaPi2b, Nectin-4, NKG2D, NOTCH3, NTAL, NY-ESO-1, p-CAD, PD-1, PDGFR, PLD3, prostate specific cancer antigen (PSCA), prostate-specific membrane antigen (PSMA), PTK7, RORI, S1, Siglec-H, SLC44A4, SLITRK6, STEAP1, STX4, TCR alpha/beta, TF, TGFB RII, TGM2, TIM-1, TLR1, TLR2, TLR6, TLR7, TLR10, TNFSF7, TROP-2, VAMPS, VEGFR, VEGF-R2, vimentin, and VPS26A.

In embodiments of the invention that include compositions that bind to a cell-free circulating effector, the cell-free circulating effectors may be a growth factor, hormone, cytokine, pathogen, virus, microbe, mutagen, or carcinogen. The two or more cell-free circulating effectors may be of the same type or of different types. A target cell may be responsive to one or more of the cell-free circulating effectors. Binding of the nucleic acid nanoparticle may alter the responsiveness of the target cell to an effector. For example, binding of the nucleic acid nanoparticle may increase or decrease the responsiveness of the target cell to an effector.

DETAILED DESCRIPTION

The invention provides a broad range of compositions that target cells to affect their function. Particularly, the invention takes advantage of nanoparticle technology, specifically DNA and/or RNA nanoparticle technology, to provide targeted delivery of cargo to one or more target cells. In some embodiments, the compositions include nucleic acid nanoparticles that serve as vehicles for delivery of functional components to cells. The functional components may be cargo molecules, such as therapeutic agents, that alter cell activity when they are internalized. Alternatively or additionally, the functional components may bind to the surface of cells to alter intracellular pathways or to alter interactions between target cells and other cells or molecules in their environment. The nucleic acid nanoparticles may include targeting moieties that bind to components of target cells to facilitate delivery of cargo or other functional components to the appropriate cell type. In some embodiments, the compositions include cargo molecules attached directly to targeting moieties. The compositions of the invention have many uses as detailed herein. A preferred usage is for delivery of different concentrations of different cancer drugs to a target cell in which the different concentrations of the different drugs are on a single nanoparticle (DNA or RNA nanoparticle).

Nucleic Acid Nanoparticles with Multiple Cargoes at Different Stoichiometries

In aspects, the invention provides compositions capable of delivering different cargoes at different amounts.

Figure 1:
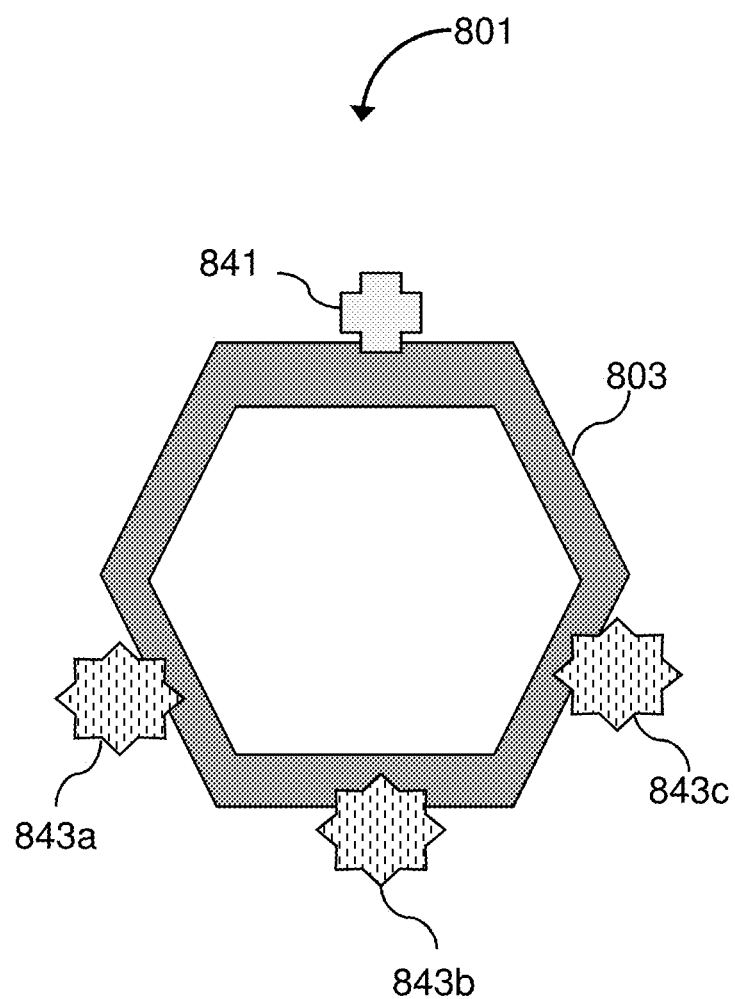
FIG. 1 illustrates a composition according to an embodiment of the invention.

FIG. 1 illustrates a composition 801 according to an embodiment of the invention. The composition 801 includes a nucleic acid nanoparticle 803 linked to a first moiety 841 and a second moiety 843a, 843b, 843c, and the first and second moieties are present on the nucleic acid nanoparticle 803 in different amounts. The nucleic acid nanoparticle 803 may be linked to a targeting moiety that facilitates delivery of the nanoparticle 803 to a target cell. The targeting moiety may bind to a target on or in a target cell.

Nanoparticle Cargo, Including Chemotherapeutics

The compositions of the invention are useful for treating cancer. Cancer is a group of diseases in which one or more types of cells proliferate in an unregulated manner and invade other parts of the body. Cancer results from genetic mutations that are either inherited or result from environmental factors. The mutations alter the activity of pathways to lead to unchecked cell growth. Although mutations in specific genes that lead to various cancers have been identified, cancers typically arise from multiple mutations. In addition, multiple pathways are dysregulated in most cancers.

Some of the major therapeutic approaches to cancer treatment include radiation therapy, surgery, and chemotherapy. However, each of those approaches has its drawbacks. Surgery is most effective when tumors are localized within the body but is not be appropriate when cancer cells have spread through the body. Even when a cancerous tumor is localized, surgery carries the risk that undetected cancer cells will not be eliminated. Radiation and chemotherapy treat cancer by killing actively proliferating cells. Unfortunately, such treatments do not discriminate between cancer cells and healthy cells, so they can have severe side effects that result from damage to normal cells that reproduce rapidly, such as cells of the gastrointestinal and immune systems.

More recently, molecular targeted therapeutic approaches have been developed to avoid the pitfall of surgery, radiation, and chemotherapy. Targeted therapy is based on delivery of a therapeutic agent specifically to cancer cells. One of the challenges of targeted therapy is how to deliver therapeutic agents at dose effective to kill malignant cells while avoiding delivery to normal cells. Another problem is that delivery of a therapeutic agent that affects a single target may not be sufficient. As indicated above, cancer typically develops from the result of aberrant activity of multiple pathways, so disrupting a single activity may not stop growth of cancer cells. In addition, due their high mutagenic rate, cancer cells can adapt to become independent of the pathway in which the target functions.

The compositions of the invention address the challenges of targeted cancer therapy in several ways. For example, some compositions allow the activity of multiple pathways to be altered with a single multifunctionalized nanoparticle. Particularly, compositions of the invention include a nucleic acid nanoparticle, a first amount of a first moiety linked to the nucleic acid nanoparticle, and a second amount of a second moiety linked to the nucleic acid nanoparticle, wherein the first and second amounts are different.

Each of the first and second moieties may be a cargo to be delivered to a cell. For example and without limitation, each of the first and second moieties may independently be a label, reporter, stabilizing agent, targeting moiety, peptide, or therapeutic agent. Therapeutic agents may be moieties may be small molecule agents, e.g., organic molecules having a mass of less than 1 kDa, 1.5 kDa, or 2 kDa, or biologic agents, e.g., agents that include proteins, peptides, antibodies, nucleic acids, and combinations thereof. The moieties may be chemotherapeutics. For example and without limitation, chemotherapeutics include actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, or vinorelbine. Additional chemotherapeutic agents are described in U.S. Publication 2017/0121708, the contents of which are incorporated herein by reference.

For diagnostic procedures, it is useful to identify target cells, such as cancer cells or infected cells. Thus, one of the moieties may be a detectable label that facilitates identification of a target cell. For example and without limitation, the label may be a fluorescent molecule, optical label, light-emitting molecule, phosphorescent molecule, dye, radiolabel, enzyme, or substrate.

In general, different agents are effective at different concentrations. Common measures for the concentration at which a therapeutic agent is effective are the $IC_{50}$ and $EC_{50}$, although other measures may be used. Consequently, when delivering multiple therapeutic agents with a single composition, it is advantageous to be able to provide the therapeutic agents in different amounts so that each agent is supplied in an amount at or near the concentration that optimizes its effectiveness. Thus, different moieties may be attached to nanoparticles in different amounts to facilitate delivery of each moiety at an optimal concentration.

The different moieties may act on the same cell. Alternatively or additionally, the different moieties may act on different cells. The different cells may be in proximity to each other. For example, the different cells may be in contact with each other, may be in the same tissue, or may otherwise be associated with each other.

The different moieties may alter the activities of different pathways. The pathways may be altered in the same cell or in different cells. The different pathways may be involved in a common disease or disorder. For example, aberrant activity in each pathway may be associated with the disease or disorder, such as cancer. The different moieties may act on cells and/or may alter activities of different pathways at different amounts.

The nanoparticle may have the first and second moieties bound at different stoichiometries. For example, the two moieties may be linked to the nanoparticle in stoichiometric ratio other than 1:1, such as 1:2, 1:3, 1:4, 1:5, 2:3, 3:4, etc.

The skilled artisan will realize that while exemplified for cancer, this approach of targeting multiple disease pathways using different amounts of different drugs applies outside of cancer. For example, any disease in which multiple pathways in a single cell need to be targeted with different drugs at different concentrations is within the scope of the invention. Other exemplary diseases include tuberculosis, leprosy, malaria, HIV/AIDS, autoimmune diseases, inflammatory diseases, e.g., Crohn's disease and inflammatory bowel disease, infections, infectious diseases, hereditary angioedema (HAE), multiple sclerosis, spinal cord injury, dyslipidemia, hypertension, neurological diseases, eg., Alzheimer's disease and Parkinson's disease, ulcers, psoriasis, and hepatitis.

Nucleic acid nanoparticles Referring to FIG. 1, a nucleic acid nanoparticle 803 forms the structural core of certain compositions of the invention. As used herein, "nanoparticle" refers to particles having dimensions that are measured on the nanometer scale. For example, a nanoparticle may have a diameter, length, width, or depth of from 1 to 1000 nm.

The nucleic acid nanoparticle 803 may be formed from RNA, DNA, or a combination of RNA and DNA. Various types of nucleic acid nanoparticles that serve as structural scaffolds have been described.

RNA nanoparticles are formed from the ordered arrangement of individual RNA molecules having defined secondary structures. RNA molecules form a variety of structural motifs, such as pseudoknots, kissing hairpins, and hairpin loops, that affect both the geometry of the molecule and its ability to form stable interactions with other RNA molecules via base pairing. Typically, individual RNA molecules have double-stranded regions that result from intramolecular base pairing and single-stranded regions that can for base pairs with other RNA molecules or can otherwise bind to other types of molecules.

A variety of RNA nanostructures having ordered two-dimensional or three-dimensional structures are known, including, for example and without limitation, nanoarrays, nanocages, nanocubes, nanoprisms, nanorings, nanoscaffolds, and nanotubes. Nanorings may be symmetrical structures that include 3, 4, 5, 6, 7, 8, or more RNA molecules arrayed around an axis. Thus, nanorings may be trimers, tetramers, pentamers, hexamers, heptamers, oxamers, or higher-numbered polymers. Nanorings may be circular, triangular, square, pentagonal, hexagonal, heptagonal, octagonal, or otherwise polygonal in shape. Other types of RNA nanoparticles, such as sheets and clusters, are also possible and within the scope of the invention. "Nanoscaffold" refers generally to a nanostructure to which other molecules can be attached. RNA nanoparticles of various structural arrangements are described in, for example, WO 2005/003,293; WO 2007/016,507; WO 2008/039,254; WO 2010/148,085; WO 2012/170,372; WO 2015/042,101; WO 2015/196,146; WO 2016/168,784; and WO 2017/197,009, the contents of each of which are incorporated herein by reference.

RNA nanoparticles may contain multiple units that are themselves RNA nanostructures. For example, RNA nanoparticles may contain two or more trimers, tetramers, pentamers, hexamers, heptamers, octamers, or other polymers. The individual units may have any structure, such as those described above.

RNA/DNA hybrid nanoparticles that allow delivery of functional RNA molecules, such as ribozymes, riboswitches, and siRNA, have also been reported. RNA/DNA hybrid nanoparticles may have structures similar to those described above for RNA nanoparticles. RNA/DNA hybrid nanoparticles in which only the arms of the nanoparticle have been reported. RNA/DNA nanoparticles of various structural arrangements are described in, for example, US 2016/0208245; WO 2008/039,254; WO 2010/148,085; WO 2013/075,132; WO 2013/075,140; WO 2014/039,809; WO 2015/042,101; WO 2015/171,827; and WO/2017/139,758, the contents of each of which are incorporated herein by reference.

DNA nanoparticles capable of carrying cargo have also been described. DNA nanoparticles may be made from dendrimers. One common strategy for making DNA nanostructures is to build structures from dendrimers that contain double-stranded central regions and unpaired, single-stranded ends. Thus, one dendrimer can interact with up to four other molecules at its unpaired ends. Serial assembly of DNA dendrimers into polymeric structures allows formation of nanoparticles having various 3-dimensional arrangements. DNA nanoparticles of various structural arrangements are described in, for example, WO 2010/017,544; WO 2010/017,544; WO 2014/153,394; WO 2017/143,156; and WO 2017/143,171, the contents of each of which are incorporated herein by reference.

Nucleic acids are important macromolecules because the sequence of bases in a nucleic acid can carry information or impart functionality to the molecule. The nucleic acid nanoparticles of the invention may contain nucleic acid molecules that have functional information contained within their sequences. Additionally or alternatively, the sequences of nucleic acid molecules in the nanoparticles may play purely structural roles in coordinating the assembly and arrangement of molecules within the nanostructure.

Nucleic acid nanoparticles may contain naturally-occurring nucleotides, or they may contain chemically-modified nucleotides. Chemically-modified nucleotides are known in the art and described in, for example, WO 2018/118587, the contents of which are incorporated herein by reference. For example and without limitation, nucleic acid aptamers may contain one or more of a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholino, and phosphorothioate modification. Other modified nucleotides include 5caC, 5fC, 5hoC, 5hmC, 5meC/5fu, 5meC/5moU, 5meC/$^{th}$G, 5moC, 5meC/5camU, 5meC, ψ, 5meC/ψ, 5moC/5moU, 5moC/5meU, 5hmC/5meU, me1ψ, 5meC/me1ψ, 5moU, 5camU, m6A, 5hmC/ψ, 5moC/ψ, me6DAP, me4C, 5fu, 5-methoxyUridine, 2-aminoadenine, 2-thiocytosine, 2-thiothymine, 2-thiouracil, 3-methyladenine, 4-thiouracil, 5,6-dehydrouracil, 5-allylcytosine, 5-allyluracil, 5-aminoallylcytosine, 5-aminoallyluracil, 5-bromouracil, 5-ethynylcytosine, 5-ethynyluracil, 5-fluorouracil, 5-hydroxymethylcytosine, 5-hydroxymethyluracil, 5-iodouracil, 5-methylcytosine, 5-methyluracil, 5-propynylcytosine, 5-propynylcytosine, 5-propynyluracil, 5-propynyluracil, 6-O-methylguanine, 6-thioguanine, 7-deaza-8-azaguanine, 7-deazaadenine, 7-deazaguanine, 7-deazaguanine, 8-oxoadenine, 8-oxoguanine, 5-methylcytidine, pseudouridine, inosine, 2'-O-methyladenosine, 2'-O-methylcytidine, 2'-O-methylguanosine, 2'-O-methyluridine, 2'-O-methyl-pseudouridine, 2'-O-methyl 3'-phosphorothioate adenosine, 2'-O-methyl 3'-phosphorothioate cytidine, 2'-O-methyl 3'-phosphorothioate guanosine, 2'-O-methyl 3'-phosphorothioate uridine, a conformationally-restricted nucleotide, and 2'-O-methyl 3'-phosphorothioate pseudouridine. Representative modified nucleotides are shown below:

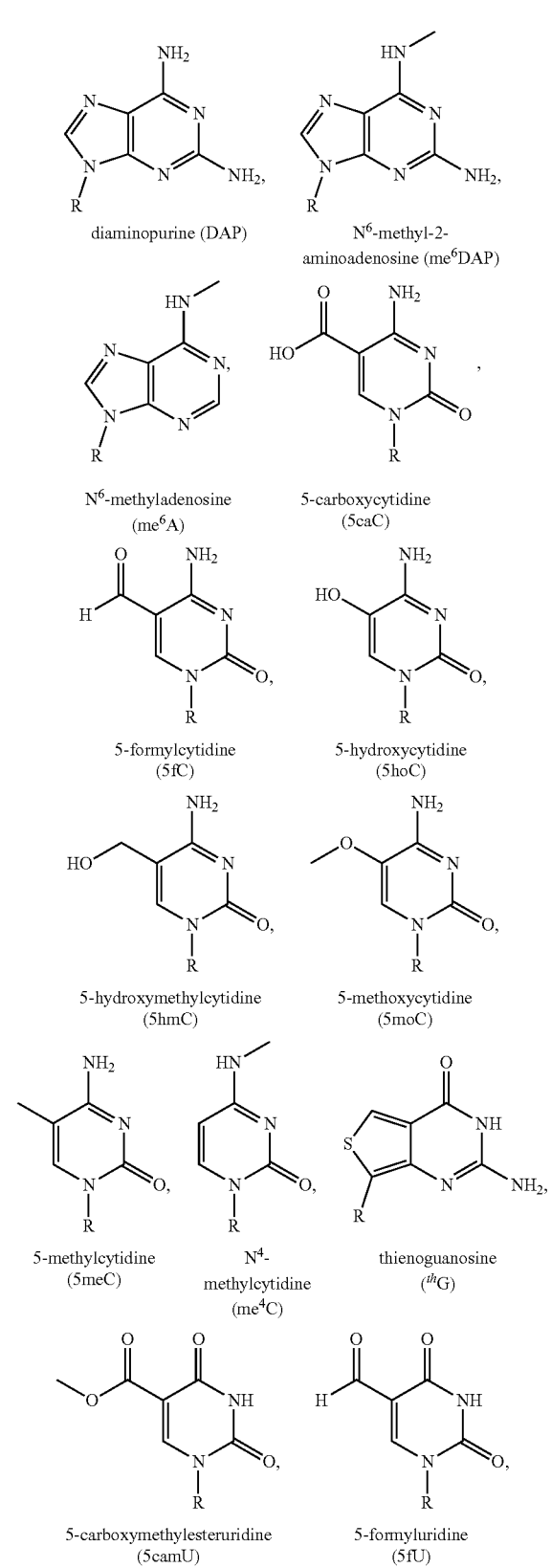

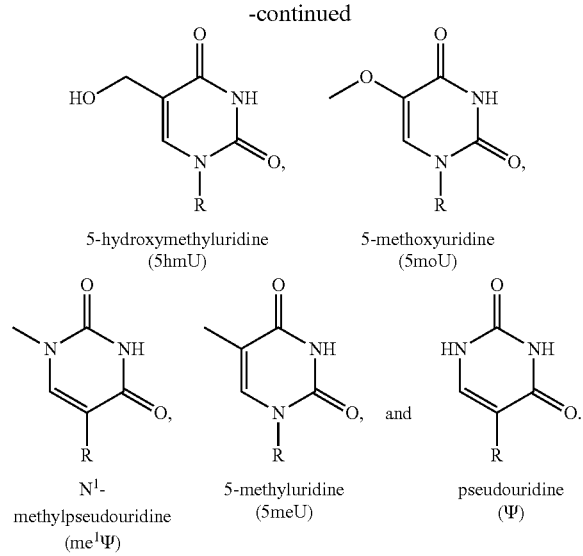

Modified nucleotides may have linkages other than phosphodiester bonds. For example, modified nucleotides may be linked by peptide, phosphorothioate, or phosphate bonds. Additionally, aptamers may contain one or more other chemical modifications described in WO 2018/118587.

Components of nucleic acid nanoparticles may be folded using DNA or RNA origami techniques to enhance stability or cell entry. DNA and RNA origami techniques are known in the art and described in, for example, U.S. Pat. No. 7,842,793; WO 2016/144755; Han et al., Single-stranded DNA and RNA origami, Science 15 Dec. 2017: Vol. 358, Issue 6369, eaao2648, DOI: 10.1126/science.aao2648, the contents of each of which are incorporated herein by reference. RNA origami is a method through which single-stranded RNA can be systematically folded into complex and molecularly defined two- and three-dimensional nanostructures using oligonucleotide hybridization and interstrand cross-overs to dictate the final shape. The use of RNA origami as a mRNA packaging system is within the scope of the invention, which contemplates exploration of its application as a therapeutic reagent both in vivo and in vitro for diagnostic, treatment, and/or research purposes for cancer and other genetically-related conditions.

Nucleic acid nanoparticles may contain additional modifications that minimize proteins or other molecules from adhering non-specifically to the nanoparticles. For example, nucleic acid nanoparticles and/or nucleic acid monomers contained therein may contain polyethylene glycol (PEG) moieties.

Targeting Moieties

The targeting moiety may be any molecule or agent that facilitates delivery of the nanoparticle to a target cell. The targeting moiety is optional, and compositions may be used in certain embodiments without a targeting moiety. However, targeted delivery in some embodiments is facilitated by a targeting moiety.

For example and without limitation, the targeting moiety may be an antibody, aptamer, ligand, nucleic acid, peptide, protein, carbohydrate, or receptor. The use of antibodies to target nanoparticles to specific cells is described, for example, in Carter, et al., Antibody-targeted nanoparticles for cancer treatment, Immunotherapy, 8(8):941-58 (2016); and Fay and Scott, Antibody-targeted nanoparticles for cancer therapy, 3(3):381-94 (2011), the contents of each of which are incorporated herein by reference. The use of aptamers to target cargo to specific cells is described in, for example, U.S. Pat. Nos. 8,883,994; 9,388,418; Zhou, et al., Cell-Specific RNA Aptamer against Human CCR5 Specifically Targets HIV-1 Susceptible Cells and Inhibits HIV-1 Infectivity, Chemistry and Biology, 22:379-90 (2015); and Shum, et al., Nucleic Acid Aptamers as Potential Therapeutic and Diagnostic Agents for Lymphoma, J. Cancer Ther., 4(4):872-890 (2013), the contents of each of which are incorporated herein by reference. The use of the carbohydrate N-acetylgalactosamine as a targeting moiety is described in, for example, Nair, Multivalent N-Acetylgalactosamine-Conjugated siRNA Localizes in Hepatocytes and Elicits Robust RNAi-Mediated Gene Silencing, J. Am. Chem. Soc., 2014, 136 (49), pp 16958-16961, DOI: 10.1021/ja505986a, the contents of which are incorporated herein by reference.

The targeting moiety may bind to a molecule on or in a target cell. For example and without limitation, the targeting moiety may bind to a cell surface protein, carbohydrate, glycoprotein, lipid, glycolipid, or other molecule. The molecule may be expressed on the surface of the target cell. For example and without limitation, the target cell may be a T cell, B cell, dendritic cell, NK cell, macrophage, platelet, erythrocyte, epithelial cell, endothelial cell, neutrophil, cancer cell, senescent cell, or stem cell.

For example and without limitation, the target molecule may be 5T4, ALDH1, alpha V beta 6 integrin, ARMX3, AXL, B2MG, BCMA, C4.4A, CA6, CA9, Cadherin 6, CAIX, carcinoembryonic antigen (CEA), CCR1, CCR10, CCR4, CCR5, CCR6, CCR8, CD1d, CD3, CD4, CD5, CD8, CD9, CD11c, CD13, CD14, CD15, CD16, CD16A, CD19, CD20, CD22, CD25, CD27, CD28, CD30, CD31, CD32, CD32B, CD33, CD34, CD37, CD38, CD39, CD41, CD44, CD44v6, CD45R, CD45RA, CD45RO, CD47, CD49b, CD51, CD54, CD56, CD57, CD61, CD62, CD62E, CD62L, CD64, CD66b, CD69, CD70, CD74, CD79B, CD79 alpha/beta, CD80, CD81, CD83, CD86, CD94/NKG2, CD103, CD117, CD119, CD123, CD127, CD133, CD134, CD137, CD138, CD146, CD154, CD160, CD161/NK1.1, CD164, CD171, CD172a, CD180, CD194, CD197, CD202b, CD205, CD206, CD207, CD215, CD223, CD235a, CD252, CD268, CD269, CD272, CD273, CD282, CD284, CD307d, CD309, CD317, CD326, CD369, CD370, c-Kit, c-MET, Criptoprotein, Crth2, CTLA-R, CXCR3, CXCR4, CXCR5, DCIR2, DEP1, DLL3, EBP50, EDG-1/S1P1, EDNRB, EFNA4, EGFR, EGFRvIII, EMR1, ENPP3, epithelial cell adhesion molecule (EpCAM), EphA2, ErbB, ErbB2, FAP, Fas ligand, FGFR2, FGFR3, fibroblast activation protein (FAP), FLT3, folate receptor-alpha, GARP, GD2, GITR, glypican 3, gp100, gpA33, GPC3, GPNMB, GUCY2C, HGF, HER2, HER3, HLA-DR, IFN-gamma R, IgG, IGF-1R, IL-1R5, IL-1 RI, IL-6R, IL-6R alpha, IL-13 receptor α, IL-18R alpha, IL-21R, IL-23R, kappa light chain, KIR Family, L1 cell adhesion molecule (L1CAM), LAMP-1, LANCL1, LAP, Lewis Y, LFA-1, LIV-1, LRRC15, MAGE family members, mesothelin, MET, MHCII, MSLN, MUC1, MUC16, NaPi2b, Nectin-4, NKG2D, NOTCH3, NTAL, NY-ESO-1, p-CAD, PD-1, PDGFR, PLD3, prostate specific cancer antigen (PSCA), prostate-specific membrane antigen (PSMA), PTK7, RORI, S1, Siglec-H, SLC44A4, SLITRK6, STEAP1, STX4, TCR alpha/beta, TF, TGFB RII, TGM2, TIM-1, TLR1, TLR2, TLR6, TLR7, TLR10, TNFSF7, TROP-2, VAMPS, VEGFR, VEGF-R2, vimentin, or VPS26A.

For example and without limitation, molecules that can be used to target immune cells include CCR1, CCR10, CCR4, CCR5, CCR6, CCR8, CD1d, CD3, CD4, CD5, CD8, CD9, CD11c, CD13, CD14, CD15, CD16, CD16A, CD19, CD20, CD22, CD25, CD27, CD28, CD30, CD31, CD32, CD32B, CD33, CD34, CD37, CD38, CD39, CD41, CD44, CD44v6, CD45R, CD45RA, CD45RO, CD47, CD49b, CD51, CD54, CD56, CD57, CD61, CD62, CD62E, CD62L, CD64, CD66b, CD69, CD70, CD74, CD79B, CD79 alpha/beta, CD80, CD81, CD83, CD86, CD94/NKG2, CD103, CD117, CD119, CD123, CD127, CD133, CD134, CD137, CD138, CD146, CD154, CD160, CD161/NK1.1, CD164, CD171, CD172a, CD180, CD194, CD197, CD202b, CD205, CD206, CD207, CD215, CD223, CD235a, CD252, CD268, CD269, CD272, CD273, CD282, CD284, CD307d, CD309, CD317, CD326, CD369, CD370, Crth2, CTLA-R, CXCR3, CXCR4, CXCR5, DCIR2, EDG-1/S1P1, EMR1, Fas ligand, GARP, GITR, HLA-DR, IFN-gamma R, IgG, IL-1R5, IL-1 RI, IL-6R, IL-6R alpha, IL-13 receptor α, IL-18R alpha, IL-21R, IL-23R, kappa light chain, KIR Family, LAMP-1, LAP, LFA-1, MHCII, NKG2D, PD-1, S1, Siglec-H TCR alpha/beta, TGFB RII, TLR1, TLR2, TLR6, TLR7, TLR10, and TNFSF7.

For example and without limitation, molecules that can be used to target cancer cells include 5T4, alpha V beta 6 integrin, AXL, BCMA, C4.4A, CA6, CA9, Cadherin 6, CAIX, carcinoembryonic antigen (CEA), CD123, CD138, CD16A, CD171, CD171, CD19, CD20, CD22, CD28, CD3, CD30, CD326 (EPCAM) CD32B, CD33, CD38, CD64, CD79B, CEA, c-Kit, c-MET, criptoprotein, CS1, DLL3, EDNRB, EFNA4, EGFR, EGFR, EGFRvIII, ENPP3, epithelial cell adhesion molecule (EpCAM), ErbB, ErbB2, erythropoietin-producing hepatocellular A2 receptor (EphA2), FAP, FGFR2, FGFR3, fibroblast activation protein (FAP), FLT3, folate receptor-alpha, GD2, glycosylated MUC-1, glypican 3, gp100, gpA33, GPC3, GPNMB, GUCY2C, HER2, HER3, IGF-1R, IL-6R, interleukin 13 receptor α (IL13Rα), kappa light chain, L1 cell adhesion molecule (L1CAM), Lewis Y, LIV-1, LRRC15, MAGE family members, mesothelin, MET, MSLN, MUC1, MUC16, NaPi2b, Nectin-4, NKG2D, NOTCH3, NY-ESO-1, p-CAD, PDGFR, prostate specific cancer antigen (PSCA), prostate-specific membrane antigen (PSMA), PTK7, RORI, SLC44A4, SLITRK6, STEAP1, TF, TIM-1, TROP-2, vascular endothelial growth factor receptor 2 (VEGF-R2), and VEGF.

For example and without limitation, molecules that can be used to target senescent cells include ARMX3, B2MG, DEP1, EBP50, LANCL1, NTAL, PLD3, STX4, VAMPS, vimentin, and VPS26A.

For example and without limitation, molecules that can be used to target stem cells include ALDH1, CD34, CD117, CD133, CD164, HGF, and TGM2.

The targeting moiety may promote delivery of the composition or a component of the composition to a subcellular location. For example, the targeting moiety may promote escape of the nanoparticle or the CRISPR component, or one of the molecules from the nanoparticle or the CRISPR component, from the endosome. Examples of compounds that may promote endosomal escape include polymers, such as polyethylenimine (PEI), poly(amidoamine)s (PAAs), charge-reversal copolymers, poly(propylacrylic acid) (PPAA) derivatives, amphiphilic cationic copolymers, and pH-sensitive degradable polymers; cationic or zwitterionic lipids; peptides, such as KALA, HALA, and hemagglutinin; lipid-coated nanoparticles, such as lipid coated calcium phosphate and liposome-polycation-DNA (LPD); and inorganic nanoparticles, such as layered double hydroxide (LDH), calcium phosphate (CaP),carbonate apatite (CAp), magnesium phosphate, manganous phosphate, and calcium carbonate. Means of facilitating endosomal escape are described in, for example, Ma, Enhancing endosomal escape for nanoparticle mediated siRNA delivery, Nanoscale, 6(12):6415-25 (2014); Guo and Huang, Nanoparticles Escaping RES and Endosome: Challenges for siRNA Delivery for Cancer Therapy, J. Nanomaterials, Volume 2011, Article ID 742895, doi:10.1155/2011/742895, the contents of each of which are incorporated herein by reference. The targeting moiety may promote delivery to the nucleus. For example, the targeting moiety may include a nuclear localization signal. The targeting moiety may contain a RNA sequence that is recognized and cleaved by the endoribonuclease Dicer. The targeting moiety may contain a peptide sequence that is recognized and cleaved by an intracellular protease. The targeting moiety may contain a nucleic that can be allosterically regulated. The targeting moiety may facilitate entry of the nanoparticle into cells. For example, the targeting moiety may be folic acid or a cell-penetrating peptide, such as penetratin, model amphipathic peptide (MAP), or Hph-1.

The nucleic acid nanoparticle may be linked to multiple copies of a targeting moiety 107. The nucleic acid nanoparticle may be linked to multiple targeting moieties. The nucleic acid nanoparticle may be linked to different targeting moieties in different amounts or stoichiometries.

Antibodies or portions thereof may be used as targeting moieties or binding moieties. For example, the targeting or binding moiety may be a complete immunoglobulin, antigen-binding fragment (Fab), Fab2, variable domain (Fv), single chain variable fragment (scFv), third-generation (3G) antibody. The antibodies may be natural monoclonal antibodies or synthetic antibodies, such as recombinant antibodies, non-immunoglobulin derived synthetic antibodies, or affimer proteins. Methods of making monoclonal antibodies are known in the art and described in, for example, Antibodies: A Laboratory Manual, Second edition, edited by Greenfield, Cold Spring Harbor Laboratory Press (2014) ISBN 978-1-936113-81-1. Methods of making synthetic antibodies are described in, for example, U.S. Publication 2014/0221253; U.S. Publication 2016/0237142; and Miersch and Sidhu, Synthetic antibodies: concepts, potential and practical considerations, Methods. 2012 August; 57(4): 486-98. doi: 10.1016/j.ymeth.2012.06.012, the contents of each of which are incorporated herein by reference.

Aptamers may be used as targeting or binding moieties. Aptamers may be made of DNA, RNA, nucleic acid analogs, or peptides. Methods of making nucleic acid aptamers are described in, for example, U.S. Publication 2009/0004644; U.S. Pat. No. 9,388,418; and Shum et al., Nucleic acid aptamers as potential therapeutics and diagnostic agents for lymphoma, J Cancer Ther. 2013 June 1; 4(4): 872-890. doi:10.4236/jct.2013.44099, the contents of each of which are incorporated herein by reference.

Nucleic acid aptamers may contain naturally-occurring nucleotides, or they may contain chemically-modified nucleotides. Chemically-modified nucleotides are known in the art and described in, for example, WO 2018/118587, the contents of which are incorporated herein by reference. For example and without limitation, nucleic acid aptamers may contain one or more of a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholino, and phosphorothioate modification. Other modified nucleotides include 5caC, 5fC, 5hoC, 5hmC, 5meC/5fu, 5meC/5moU, 5meC/$^{th}$G, 5moC, 5meC/5camU, 5meC, ψ, 5meC/ψ, 5moC/5moU, 5moC/5meU, 5hmC/5meU, me1ψ, 5meC/me1ψ, 5moU, 5camU, m6A, 5hmC/ψ, 5moC/ψ, me6DAP, me4C, and 5fu. Representative modified nucleotides are shown below:

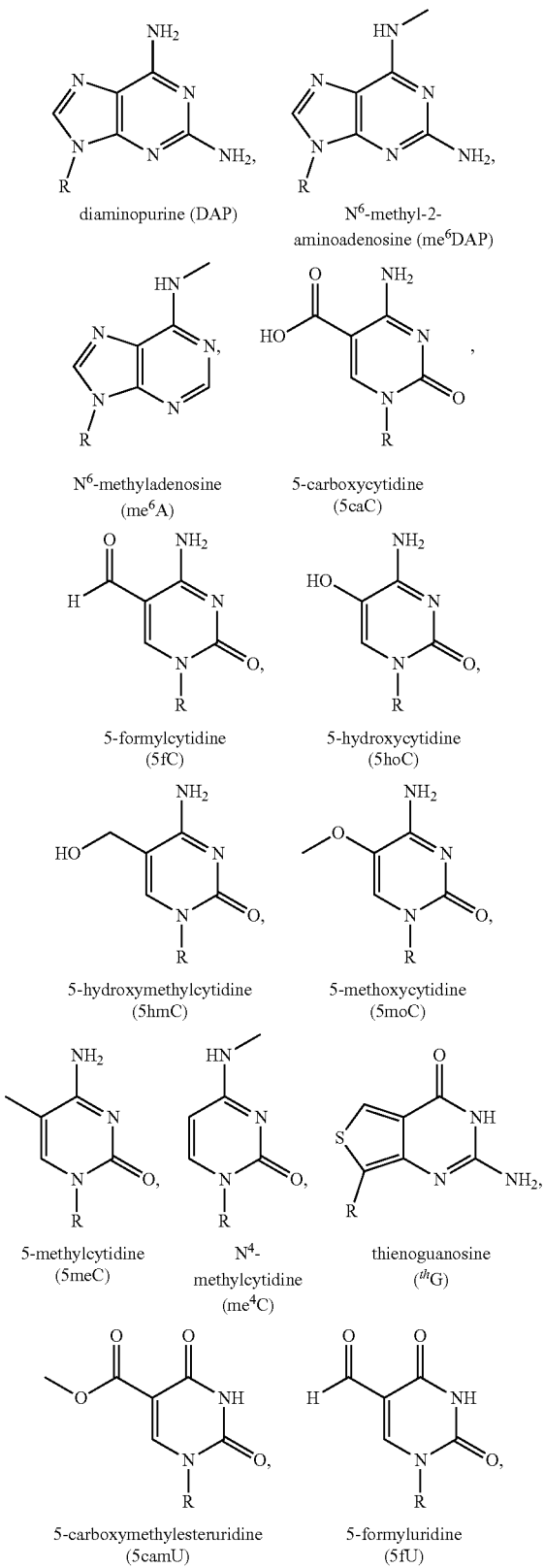

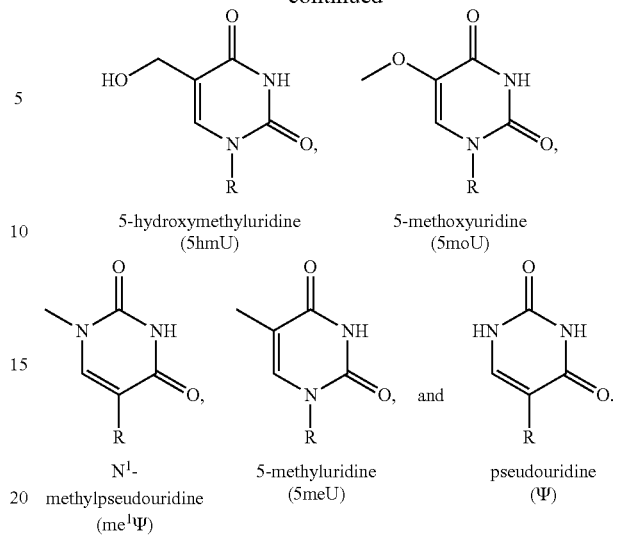

Additionally, aptamers may contain one or more other chemical modifications described in WO 2018/118587.

Nucleic acid aptamers may be folded using DNA or RNA origami techniques to enhance stability or cell entry. DNA and RNA origami techniques are known in the art and described in, for example, U.S. Pat. No. 7,842,793; WO 2016/144755; Han et al., Single-stranded DNA and RNA origami, Science 15 Dec. 2017: Vol. 358, Issue 6369, eaao2648, DOI: 10.1126/science.aao2648, the contents of each of which are incorporated herein by reference.

Aptamers may be designed and/or selected to have desirable properties beyond the ability to bind to a particular target. For example, aptamers that promote internalization of cargo into a target cell after the aptamer binds to its target on the cell surface may be used in nanoparticles of the invention. Aptamers may be designed to have such desirable properties. Alternatively or additionally, aptamers may be synthesized and empirically tested, and aptamers that have such desirable properties may be selected for use in nanoparticles of the invention.

Targeting moieties, such as aptamers may function via pattern recognition strategies. In a sequential recognition approach, targeting moieties such as aptamers are positioned on top of each other and/or on one arm of the nanoparticle. When the first targeting moiety binds to its ligand, it exposes the next targeting moiety. Sequential binding of more than one targeting moiety is required for the nanoparticle to enter the cell. In a non-sequential recognition approach, targeting moieties are positioned on different arms on the nanoparticle, and more than one targeting moiety must recognize its ligand for the nanoparticle to enter the cell Attachment of Cargo and/or Targeting Moieties to Nucleic Acid Nanoparticles Cargo and/or targeting moieties may be attached to nanoparticles by any suitable means. Non-limiting examples are provided below. In one method, monomeric nucleic acids within a nucleic acid nanoparticle may contain poly(U) stretches that are complementary to the poly(A) tails of mRNA. In another method, a DNA oligonucleotide can be used as bridge between a nucleic acid particle scaffold and the 3' end of mRNA via splint ligation. In another method, a nucleic acid particle scaffold may be modified by 5' adenylation and ligated to the 3' end of mRNA using a ligase, such as T4 DNA ligase. In another method, a free guanine base at the 3' end of RNA may be modified to contain free primary amines. For example, guanine can be modified to 8-aminohexyl guanine derivative by using N-bromosuccinimide. The primary amines can then react with a therapeutic mRNA-FRET or peptide system by, for example, using 1-Ethyl-3-(3-dimethylaminopropyl)-carbodiimide and/or N-hydroxysuccinimide. In another method, copper-free click chemistry may be used to join the cargo and/or targeting moiety to the nucleic acid scaffold.

Nucleic Acid Nanoparticles for Delivery of CRISPR Components

In other aspects, the invention provides compositions that include a nanoparticle and another type of cargo for delivery to a cell. In certain embodiments, the invention provides a composition including a nucleic acid nanoparticle, and at least one CRISPR component linked to the nucleic acid nanoparticle.

Figure 2:
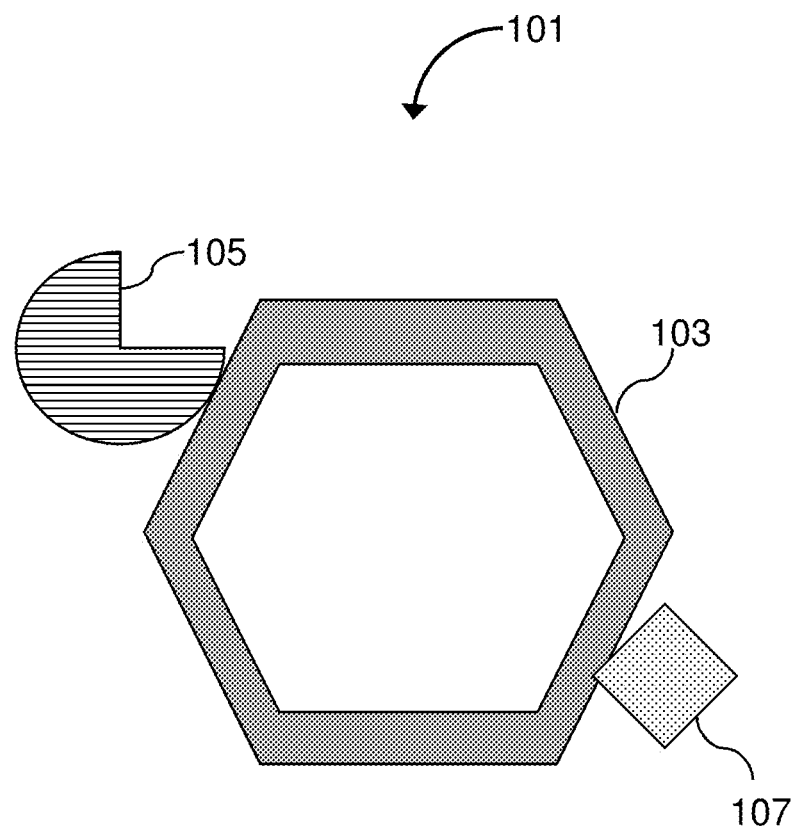
FIG. 2 illustrates a composition according to an embodiment of the invention.

FIG. 2 illustrates a composition 101 according to an embodiment of the invention. The composition 101 includes a nucleic acid nanoparticle 103 linked to a component 105 of the Clustered Regularly Interspaced Short Palindromic Repeats (CRISPR) system. The nucleic acid nanoparticle 103 may be linked to a targeting moiety 107 that facilitates delivery of the nanoparticle 103 to a target cell. The targeting moiety 107 may bind to a target on or in a target cell.

CRISPR Components

The CRISPR system is a prokaryotic immune system that provides acquired immunity against foreign genetic elements, such as plasmids and phages. CRISPR systems include one or more CRISPR-associated (Cas) proteins that cleave DNA at clustered, regularly-interspersed palindromic repeat (CRISPR) sequences. Cas proteins include helicase and exonuclease activities, and these activities may be on the same polypeptide or on separate polypeptides. Cas proteins are directed to CRISPR sequences by RNA molecules. A CRISPR RNA (crRNA) binds to a complementary sequence in the target DNA to be cleaved. A transactivating crRNA (tracrRNA) binds to both the Cas protein and the crRNA to draw the Cas protein to the target DNA sequence. Not all CRISPR systems require tracrRNA. In nature crRNA and tracrRNA occur on separate RNA molecules, but they also function when contained a single RNA molecule, called a single guide RNA or guide RNA (gRNA). The one or more RNAs and one or more polypeptides assemble inside the cell to form a ribonucleoprotein (RNP). CRISPR systems are described, for example, in van der Oost, et al., CRISPR-based adaptive and heritable immunity in prokaryotes, Trends in Biochemical Sciences, 34(8):401-407 (2014); Garrett, et al., Archaeal CRISPR-based immune systems: exchangeable functional modules, Trends in Microbiol. 19(11):549-556 (2011); Makarova, et al., Evolution and classification of the CRISPR—Cas systems, Nat. Rev. Microbiol. 9:467-477 (2011); and Sorek, et al., CRISPR-Mediated Adaptive Immune Systems in Bacteria and Archaea, Ann. Rev. Biochem. 82:237-266 (2013), the contents of each of which are incorporated herein by reference.

CRISPR-Cas systems have been placed in two classes. Class 1 systems use multiple Cas proteins to degrade nucleic acids, while class 2 systems use a single large Cas protein. Class 1 Cas proteins include Cas10, Cas10d, Cas3, Cas5, Cas8a, Cmr5, Cse1, Cse2, Csf1, Csm2, Csx11, Csy1, Csy2, and Csy3. Class 2 Cas proteins include C2c1, C2c2, C2c3, Cas4, Cas9, Cpf1/Cas12a, and Csn2.

CRISPR-Cas systems are powerful tools because they allow gene editing of specific nucleic acid sequences using a common protein enzyme. By designing a guide RNA complementary to a target sequence, a Cas protein can be direct to cleave that target sequence. In addition, although naturally-occurring Cas proteins have endonuclease activity, Cas proteins have been engineered to perform other functions. For example, endonuclease-deactivated mutants of Cas9 (dCas9) have been created, and such mutants can be directed to bind to target DNA sequences without cleaving them. dCas9 proteins can then be further engineered to bind transcriptional activators or inhibitors. As a result, guide sequences can be used to recruit such CRISPR complexes to specific genes to turn on or off transcription. Thus, these systems are called CRISPR activators (CRISPRa) or CRISPR inhibitors (CRISPRi). CRISPR systems can also be used to introduce sequence-specific epigenetic modifications of DNA, such acetylation or methylation. The use of modified CRISPR systems for purposes other than cleavage of target DNA are described, for example, in Dominguez, et al., Beyond editing: repurposing CRISPR—Cas9 for precision genome regulation and interrogation, Nat. Rev. Cell Biol. 17(1):5-15 (2016), which is incorporated herein by reference.

The compositions of the invention may include any component of a CRISPR system, such as those described above. For example and without limitation, the CRISPR component may be one or more of a helicase, endonuclease, transcriptional activator, transcriptional inhibitor, DNA modifier, gRNA, crRNA, or tracrRNA. The CRISPR component may contain a nucleic acid, such as RNA or DNA, a polypeptide, or a combination, such as a RNP. The CRISPR nucleic acid may encode a functional CRISPR component. For example, the nucleic acid may be a DNA or mRNA. The mRNA may be complexed with antisense DNA to stabilized the mRNA. The CRISPR nucleic acid may itself be a functional component, such as a gRNA, crRNA, or tracrRNA. Nucleic acid-based CRISPR components may contain modified nucleotides, such as those described elsewhere in this application. Nucleic acid-based CRISPR components may be folded using DNA or RNA origami techniques to enhance stability or cell entry.

The CRISPR component may alter expression of a target in a cell. For example, the CRISPR component may increase or decrease expression of a target in a cell.

The component 105 the CRISPR system may be linked to the nucleic acid nanoparticle by any suitable means. The linkage may be via covalent or non-covalent bond. The nanoparticle may have one or more single-stranded "toeholds" that form base pairs with the CRISPR component. The CRISPR component may be attached via a cleavable linker, such as a bond that can be cleaved by light, an enzyme, pH, or other mechanism. Thus, the composition may be tunable to allow release of the CRISPR component under specific conditions or in a particular location.

The composition may include an element that induces expression of the CRISPR component. For example, expression of the CRISPR component may be induced by an antibiotic, such as tetracycline, or other chemical. Inducible CRISPR systems have been described, for example, in Rose, et al., Rapidly inducible Cas9 and DSB-ddPCR to probe editing kinetics, Nat. Methods, 14, pages 891-896 (2017); andCao, et al., An easy and efficient inducible CRISPR/Cas9 platform with improved specificity for multiple gene targeting, Nucleic Acids Res. 14(19):e149 (2016). The inducible element may be part of the CRISPR component 105, or it may be a separate component attached to nucleic acid nanoparticle 103.

The nucleic acid nanoparticle 103 may be linked to multiple copies of a CRISPR component 105. The nucleic acid nanoparticle 103 may be linked to multiple CRISPR components 105. The nucleic acid nanoparticle 103 may be linked to different CRISPR components 105 in different amounts or stoichiometries.

Safety switches Introduction of a CRISPR component that can alter gene expression in a target cell carries the risk that the CRISPR component will cause deleterious effects in a sub-population of cells. Therefore, it is advantageous to include a mechanism for killing cells in which the CRISPR component is producing undesirable effects, i.e., a "safety switch" or "suicide switch". Thus, compositions may include a safety switch. The safety switch may be provided a nucleic acid linked to the nucleic acid nanoparticle.

One example of a safety switch is an inducible caspase-9 (iCasp9) gene. Caspase-9 is a protease that initiates apoptotic pathways, leading to cell death. Caspase-9 is synthesized as an inactive, pro-enzyme monomer, but dimerization results in a cleavage event that converts caspase-9 into its enzymatically active form. Active caspase-9 then cleaves other targets to trigger apoptosis. iCasp9 systems include caspase-9 fused to another protein, such as FKBP, that dimerizes in the presence of a small molecule drug. Consequently, cells that express iCasp9 are viable under normal condition but can be selectively killed by addition of the drug. iCasp9 systems are described in, for example, Straathof et al., An inducible caspase 9 safety switch for T-cell therapy, Blood 105(11):4247-4254 (2005), doi: 10.1182/blood-2004-11-4564; and Gargett and Brown, The inducible caspase-9 suicide gene system as a "safety switch" to limit on-target, off-tumor toxicities of chimeric antigen receptor T cells, Front. Pharmacol. 5:235(2014), doi: 10.3389/fphar.2014.00235, the contents of each of which are incorporated herein by reference. Other examples of safety switches include herpes simplex virus-thymidine kinase (HSV-TK) and EGFR-human folate receptor 1 (EGR-FOLR1), CD20, and caspase-8, described in, for example, Recchia et al. (2006) Retroviral vector integration deregulates gene expression but has no consequence on the biology and function of transplanted T cells. Proc. Natl. Acad. Sci. U.S.A. 103 1457-1462. 10.1073/pnas.0507496103; Ciceri et al. (2009) Infusion of suicide-gene-engineered donor lymphocytes after family haploidentical haemopoietic stem-cell transplantation for leukaemia (the TK007 trial): a non-randomised phase I-II study. Lancet Oncol. 10 489-500. 10.1016/S1470-2045(09)70074-9; and Wu et al., A Fusion Receptor as a Safety Switch, Detection, and Purification Biomarker for Adoptive Transferred T Cells, Mol Ther. 2017 Oct. 4; 25(10):2270-2279. doi: 10.1016/j.ymthe.2017.06.026; van Loenen et al., Multi-cistronic vector encoding optimized safety switch for adoptive therapy with T-cell receptor-modified T cells, Gene Ther. 2013 August; 20(8):861-7. doi: 10.1038/gt.2013.4; Khaleghi, Sepideh & Rahbarizadeh, Fatemeh & Ahmadvand, Davoud & Rassaee, Mohammad & Pognonec, Philippe. (2012). A caspase 8-based suicide switch induces apoptosis in nanobody-directed chimeric receptor expressing T cells. International journal of hematology. 95. 434-44. 10.1007/s12185-012-1037-6, the contents of each of which are incorporated herein by reference.

Disorders and Conditions

CRISPR-containing compositions of the invention are useful for treating any genetic disease, disorder, or condition. For example, they are useful for treating various types of cancer, such as those described in U.S. Publication 2018/0028686, which is incorporated herein by reference. CRISPR-containing compositions of the invention may be used to treat other types of genetic diseases, disorders, or conditions. For example and without limitation, the disease, disorder, condition may be ADA-SCID, adrenoleukodystrophy (ALD), alpha-mannosidosis, Barth syndrome, beta-thalassemia, brain disorder, cardiovascular disease, central nervous system disorder, cystic fibrosis, Dentatorubro-Pallidoluysian atrophy (DRPLA). Duchenne muscular dystrophy, familial essential thrombocythaemia (ET) Fanconi anemia, fragile X syndrome (FRAXA); fragile X-associated tremor/ataxia syndrome (FXTAS); fragile XE mental tetardation (FRAXE); Friedreich ataxia (FRDA); genetic lysosomal storage disease hematologic condition, hemophilia, hereditary tyrosinemia, HIV/AIDS, Huntington Disease (HD); immunodeficiency disorder, infectious disease, inflammation, Krabbe disease, leukodystrophy, metachromatic leukodystrophy (MLD), myeloproliferative neoplasm, myotonic dystrophy (DM), non-polyglutamine disorder, nucleotide repeat expansion disorder, ocular disease, polycythemia vera (PCV), polyglutamine disorders, progressive myoclonus epilepsy, SCID, SCID-X1, sickle cell anemia, skin disorder, spinobulbar muscular atrophy (SBMA), spinocerebellar ataxia, Wiskott-Aldrich syndrome, or X-linked CGD.

Compositions for Delivery of Chimeric Antigen Receptors

In other aspects, the invention provides compositions for delivery of nucleic acids that promote expression of chimeric antigen receptors in immune cells.

Figure 3:
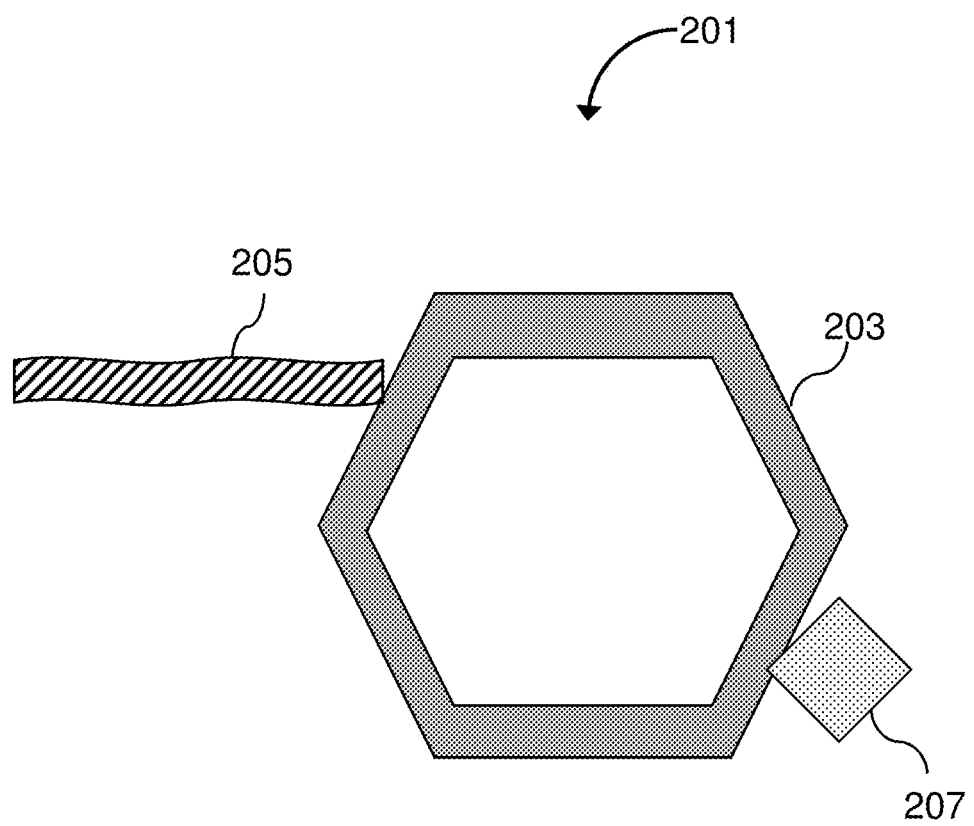
FIG. 3 illustrates a composition according to an embodiment of the invention.

FIG. 3 illustrates a composition 201 according to an embodiment of the invention. The composition 201 includes a nucleic acid nanoparticle 203 linked to a nucleic acid 205 that promotes expression of a chimeric antigen receptor in an immune cell. The nucleic acid nanoparticle 203 may be linked to a targeting moiety 207 that facilitates delivery of the nanoparticle 203 to an immune cell. The targeting moiety 207 may bind to a target on or in an immune cell. The nucleic acid nanoparticle 203 may also be linked to a CRISPR component, such as those described above.

Figure 4:
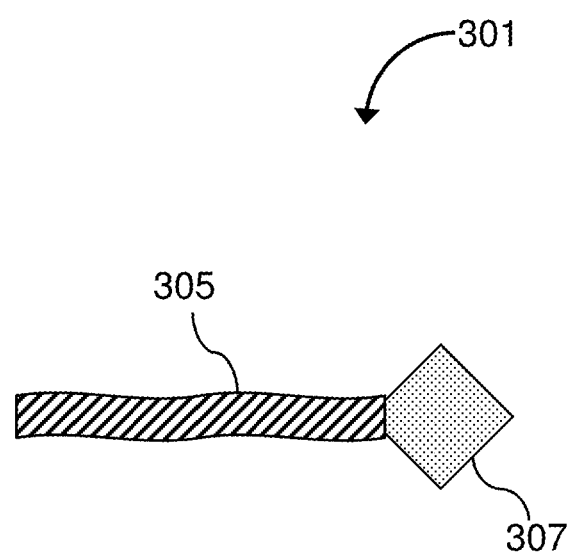
FIG. 4 illustrates a composition according to an embodiment of the invention.

FIG. 4 illustrates a composition 301 according to an embodiment of the invention. The composition includes a nucleic acid 305 that promotes expression of a chimeric antigen receptor in an immune cell. The nucleic acid 305 is linked to a targeting moiety 307. The targeting moiety 307 may bind to a target on or in a target cell. Examples of nucleic acids 305 that promote expression of a chimeric antigen receptor and targeting moieties 307 are described above. The targeting moiety 307 or the nucleic acid 305 may be linked to a safety switch, such as those described above.

Chimeric Antigen Receptors

Chimeric antigen receptors (CARs) are engineered receptors that can confer a desired specificity onto an immune cell, such as a T cell. Typically, CARs are designed to bind to molecular markers on cancer cells, such as a tumor associated antigen (TAA). CAR-expressing T cells (CAR-T cells) are useful in treating cancer because they allow rapid generation of a population of T cells that target and kill specific tumor cells. CAR-T cells can also be programmed to destroy cells infected with a pathogen, such as a virus or bacterium. CAR-T cells can be made by introducing a CAR either into a patient's own T cells (autologous CAR-T cells) or into a T cells from another donor (allogeneic CAR-T cells). CARs may also be expressed in other cells of the immune system, such as NK cells, NKT cells or macrophages. The use of CARs in cancer immunotherapy is described in, for example, Smith et al., Chimeric antigen receptor (CAR) T cell therapy for malignant cancers: Summary and perspective, J. Cellular Immnother. 2:59-68 (2016), doi.org/10.1016/j.jocit.2016.08.001; and Ye et al., Engineering chimeric antigen receptor-T cells for cancer treatment, Mol. Cancer, 17:32 (2018), doi.org/10.1186/ s12943-018-0814-0, the contents of each of which are incorporated herein by reference.

Structurally, CARs include an extracellular domain that binds to an antigen, a transmembrane domain, and an intracellular signaling domain. The extracellular domain of a CAR is typically derived from a single-chain variable fragment (scFv) of an immunoglobulin. The transmembrane domain links the scFv extracellular antigen-binding domain to the intracellular signaling domain and may be derived from CD28. The intracellular domain includes a CD3-zeta chain and may contain additional co-stimulatory domains derived from other signaling molecules. For example and without limitation, the intracellular domain may include portions from one or more of 4-1BB, CD27, CD28, CD134, CD137, CD70, CD80, CD86, and OX40. The intracellular domain may also interact with nuclear factor of activated T cell (NFAT) to induce expression of a cassette of IL-12 genes in a mechanism called T cell redirected for universal cytokine killing (TRUCK).

The chimeric antigen receptor may recognize a molecular marker associated with cancer or a tumor. The marker may be a protein or other molecule that is expressed only in tumor cells or that is expressed to higher levels in tumor cells. For example and without limitation, the chimeric antigen receptor may recognize 5T4, alpha V beta 6 integrin, AXL, BCMA, C4.4A, CA6, CA9, Cadherin 6, CAIX, carcinoembryonic antigen (CEA), CD123, CD138, CD16A, CD171, CD171, CD19, CD20, CD22, CD28, CD3, CD30, CD326 (EPCAM) CD32B, CD33, CD38, CD64, CD79B, CEA, c-Kit, c-MET, criptoprotein, CS1, DLL3, EDNRB, EFNA4, EGFR, EGFR, EGFRvIII, ENPP3, epithelial cell adhesion molecule (EpCAM), ErbB, ErbB2, erythropoietin-producing hepatocellular A2 receptor (EphA2), FAP, FGFR2, FGFR3, fibroblast activation protein (FAP), FLT3, folate receptor-alpha, GD2, glycosylated MUC-1, glypican 3, gp100, gpA33, GPC3, GPNMB, GUCY2C, HER2, HER3, IGF-1R, IL-6R, interleukin 13 receptor α (IL13Rα), kappa light chain, L1 cell adhesion molecule (L1CAM), Lewis Y, LIV-1, LRRC15, MAGE family members, mesothelin, MET, MSLN, MUC1, MUC16, NaPi2b, Nectin-4, NKG2D, NOTCH3, NY-ESO-1, p-CAD, PDGFR, prostate specific cancer antigen (PSCA), prostate-specific membrane antigen (PSMA), PTK7, RORI, SLC44A4, SLITRK6, STEAP1, TF, TIM-1, TROP-2, vascular endothelial growth factor receptor 2 (VEGF-R2), or VEGF. The chimeric antigen receptor may recognize a neoantigen, i.e., a protein or other molecule that is expressed in a mutant form in tumor cells.

In embodiments of the invention, the nucleic acid nanoparticle 203 is linked to a nucleic acid 205 that promotes expression of another type of antigen-binding molecule in an immune cell. For example, another type of engineered receptor to detect markers on tumor cells or infected cells is based on the Notch receptor. Synthetic Notch (synNotch) receptors include an extracellular recognition domain, such as scFv, a regulatory domain from the intercellular signaling receptor Notch, and a synthetic intracellular domain that can induce downstream transcription. When the extracellular domain of synNotch on the surface of a T cell binds a specific antigen on a tumor cell, the intracellular domain of the synNotch receptor is cleaved and released into the nucleus of the T cell to activate expression of target genes and induce an antitumor response. SynNotch receptors are described in Morsut et al, Engineering customized cell sensing and response behaviors using synthetic notch receptors. Cell, 164:780-91 (2016), the contents of which are incorporated herein by reference.

The CAR or other antigen-binding molecule may recognize a molecular marker associated with an infection. The marker may be a protein or other molecule that is expressed by an infectious agent, such as a virus, bacterium, or fungus, but not in the host.

The CAR or other antigen-binding molecule may recognize a multi-molecular complex. For example, the CAR may recognize a complex comprising a peptide presented by a HLA marker. The peptide may be marker for cancer, a tumor, or an infection.

Compositions that promote expression of CARs are useful in treating a variety of diseases, disorder, and conditions. For example, they are useful for treating various types of cancer, such as those described in U.S. Publication 2018/0028686, which is incorporated herein by reference. CAR-related compositions may be used to treat pathogenic infections. The pathogen may be a virus, bacterium, or fungus. For example and without limitation, the pathogen may be *Microsporum, Trichophyton, Epidermophyton, Sporothrix schenckii, Cryptococcus neoformans, Coccidioides immitis, Histoplasma capsulatum, Blastomyces dermatitidis, Candida albicans*, human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, blue tongue virus, *Bacillus anthracis, Streptococcus agalactiae, Legionella pneumophilia, Streptococcus pyogenes, Escherichia coli, Neisseria gonorrhoeae, Neisseria meningitidis, Pneumococcus* spp., *Hemophilis influenzae* B, *Treponema pallidum*, Lyme disease spirochetes, *Pseudomonas aeruginosa, Mycobacterium leprae, Brucella abortus, Mycobacterium tuberculosis* or a *Mycoplasma*. CAR-related compositions may be used to treat an inflammatory or autoimmune disease. Examples of inflammatory or autoimmune diseases include allergies, arthritis, asthma, autoimmune encephalitis, Celiac disease. colitis, or Crohn's disease, fibromyalga, inflammatory bowel disease, irritable bowel syndrome, lupus, mastocytosis, psoriasis, and rheumatoid arthritis.

Immune Cells

CARs, TCRs, and other antigen-binding molecules may be expressed in any immune cell, a cell of lymphoid or myeloid lineage. Typically, CARs are expressed in T cells or a subpopulation of T cells. However, CARs can be expressed in a T cell, T regulatory ($T_{reg}$) cell, memory T cell, effector memory T cell, central memory T cell, naïve T cell, cytotoxic T cell, gamma delta T cell, B cell, natural killer (NK) cell, natural killer T (NKT) cell, megakaryocyte, platelet, erythroblast, erythrocyte, myeloblast, monoblast, monocyte, macrophage, dendritic cell, neutrophil, basophil, eosinophil, or precursor of any of the aforementioned cells.

Sub-populations of immune cells may be identified based on the expression of one or more surface proteins or other markers. Thus, CARs of the invention may be expressed in immune cells that express one or more of CD3, CD4, CD8, CD25, and CD56.

The compositions may be used to promote expression of CARs for adoptive cell therapy. Thus, the compositions may be used to express a CAR in a cell or population of cells isolated from a subject. The cells that express the CAR may then be re-introduced into the subject.

The nucleic acid 205 may promote expression of a CAR by any mechanism. The nucleic acid may encode the CAR. Additionally or alternatively, the nucleic acid may regulate expression of the CAR. For example, the nucleic acid may be a CRISPR component that promotes expression of the CAR. The nucleic acid may be DNA or RNA. The RNA may be mRNA, crRNA, tracrRNA, gRNA, siRNA, shRNA, or miRNA. The mRNA may be complexed with antisense DNA to stabilized the mRNA. The DNA may be closed-ended linear duplex (CELiD) DNA. The nucleic acid 205 may contain modified nucleotides, such as those described elsewhere in this application. The nucleic acid 205 may be folded using DNA or RNA origami techniques to enhance stability or cell entry.

The nucleic acid nanoparticle 203 may be linked to multiple copies of a nucleic acid 205 that promotes expression of a CAR in an immune cell. The nucleic acid nanoparticle 203 may be linked to multiple nucleic acids 205 that promote expression of different CARs in an immune cell. The nucleic acid nanoparticle 205 may be linked to different nucleic acids 205 in different amounts or stoichiometries.

The use of multiple CARs that recognize different targets is useful for treating cancer. Many tumors evolve rapidly with high mutation rates. Additionally, tumors may adapt to escape surveillance by altering expression of molecules that can be recognized by the immune system. Consequently, the use of multiple CARs that recognize different tumor antigens decreases the likelihood that a tumor will evade CAR-based immunotherapies. See, e.g. Chen et al., A compound chimeric antigen receptor strategy for targeting multiple myeloma, Leukemia, 32:402-412 (2018), doi:10.1038/leu.2017.302, the contents of which are incorporated herein by reference. Thus, nanoparticles that are linked to nucleic acids that promote expression of two different CARs may be advantageous for adoptive cell transfer.

The nucleic acid nanoparticle 203 may be linked to multiple copies of a targeting moiety 207. The nucleic acid nanoparticle 203 may be linked to multiple targeting moieties 107. The nucleic acid nanoparticle 203 may be linked to different targeting moieties 207 in different amounts or stoichiometries.

The nucleic acid nanoparticle 203 may be linked to additional cargo. The cargo may be any biologically active molecule. For example and without limitation, the nucleic acid nanoparticle may be linked to a label, reporter, stabilizing agent, targeting moiety, peptide, or therapeutic agent. Examples of therapeutic agents are provided in, for example, WO 2015/042101 and WO 2017/197009, the contents of each of which are incorporated herein by reference.

Introduction of a CAR into immune cells carries the risk that the CAR directs the immune cell to kill cells other than cancer cells or infected cells. Therefore, it may be advantageous to introduce a safety switch, as described above, along with the CAR. Thus, the composition may include a safety switch linked to the nanoparticle. The safety switch may be provided as a nucleic acid, e.g., RNA or DNA, that encodes a safety switch. For example and without limitation, the safety switch may be iCasp9, HSV-TK, EGR-FOLR1, or CD20.

RNA Nanoparticles for Delivery of DNA and mRNA

In other aspects, the invention provides compositions for delivery of nucleic acids that promote expression of any gene product in a target cell.

Figure 5:
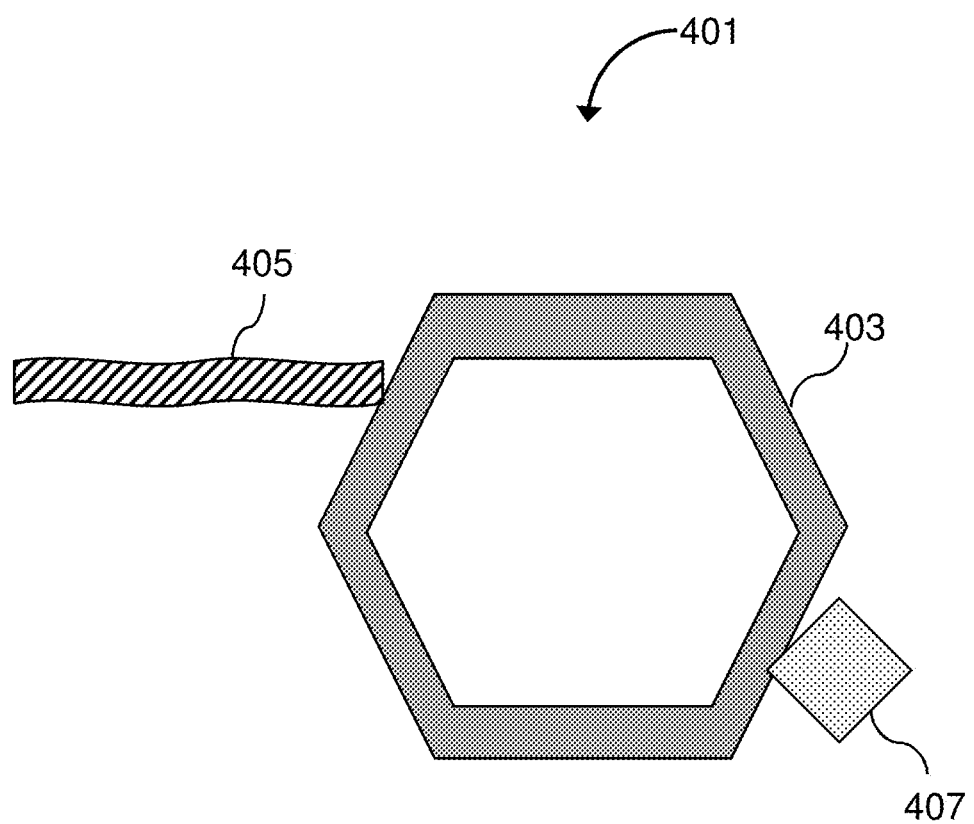
FIG. 5 illustrates a composition according to an embodiment of the invention.

FIG. 5 illustrates a composition 401 according to an embodiment of the invention. The composition 401 includes a RNA nanoparticle 403 linked to a nucleic acid 405 encoding a gene product that is expressed in a target cell. The RNA nanoparticle 403 may be linked to a targeting moiety 407 that facilitates delivery of the nanoparticle 403 to a target cell. The targeting moiety 407 may bind to a target on or in a target cell. Examples of RNA nanoparticles 403 and nucleic acids 405 that encode a gene product that is expressed in a target cell are described above. The RNA nanoparticle may be linked to a safety switch, such as those described above. The RNA nanoparticle may contain modified nucleotides, such as those described elsewhere in this application. Components of the RNA nanoparticle may be folded using DNA or RNA origami techniques to enhance stability or cell entry.

The gene product may be a polypeptide or RNA. The gene product may alter the function of the target cell. The gene product may serve as a marker or label to identify the target cell. For example and without limitation, the gene product may be a CRISPR component, a chimeric antigen receptor, or a neoantigen.

For identification and destruction of tumor cells or infected cells, it is useful to introduce a neoantigen into a target cell. For example, a tumor cell or infected cell may express a marker that is unstable or susceptible to mutation that allows it to evade the host immune system. As described above, the ability to detect multiple antigens on a target increases the likelihood that the target cell can be killed by the host immune system. Thus, introduction of a neoantigen into a target cell provides a second marker that the host immune system can use to identify the target cell. For example, the targeting moiety 407 may bind to a first marker on a tumor cell or infected cell, and the nucleic acid 405 may encode a neoantigen that serves as an additional marker for the target cell.

The RNA nanoparticle 403 may be linked to multiple copies of the targeting moiety 407. The nucleic acid nanoparticle 403 may be linked to multiple targeting moieties 407. The nucleic acid nanoparticle 403 may be linked to different targeting moieties 407 in different amounts or stoichiometries.

Multivalent Nucleic Acid Nanoparticles

In other aspects, the invention provides compositions having moieties that bind targets on different cells and facilitate the association of those cells with one another.

Figure 6:
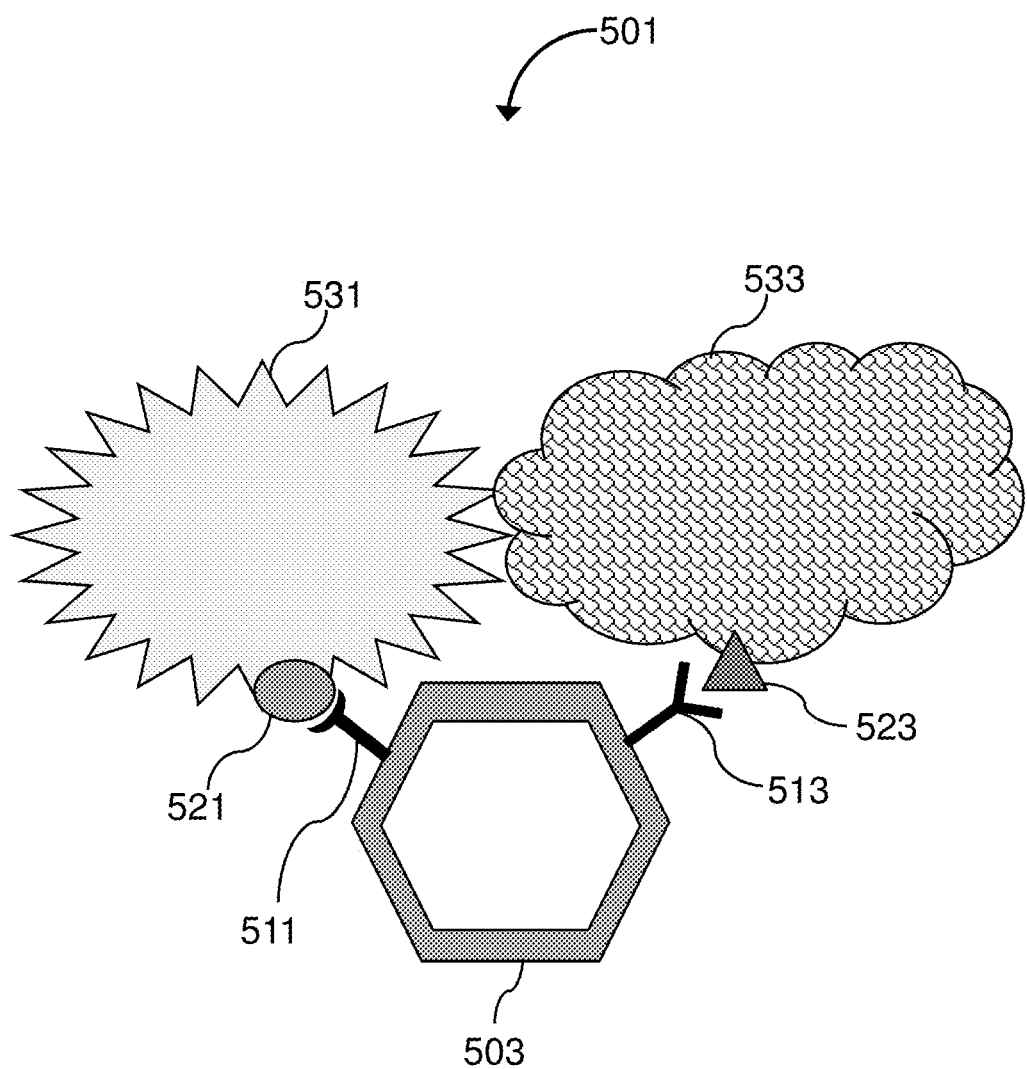
FIG. 6 illustrates a composition according to an embodiment of the invention.

FIG. 6 illustrates a composition 501 according to an embodiment of the invention. The composition 501 includes a nucleic acid nanoparticle 503 linked to a binding moiety 511 that binds to a target 521 on a target cell 531. The nucleic acid nanoparticle 503 is also linked to another binding moiety 513 that binds to another target 523 on a different target cell 533. Binding of the target moieties 511 and 513 to their respective targets 521 and 523 brings the target cells 531 and 533 into association with each other. The nucleic acid nanoparticle may be linked to additional binding moieties that bind to additional targets. The additional targets may be located on one of the target cells 531 and 533. Binding of multiple targets on the same cell may increase the avidity of the nucleic acid nanoparticle 503 for the target cell and facilitate the association the two target cells 531 and 533.

Binding Moieties and Targets

The binding moieties 511 and 513 may be any molecules or agents that allow the nucleic acid nanoparticle 503 to bind the target cells 531 and 533. For example and without limitation, each targeting moiety may independently be an antibody, aptamer, ligand, nucleic acid, peptide, protein, or receptor. These components are described above in relation to targeting moieties.

The targets 521 and 533 may be any proteins or molecules on or in the target cells 531 and 533. For example and without limitation, each of the targets may independently be a protein, carbohydrate, glycoprotein, lipid, glycolipid, or other molecule. The target may be expressed on the surface of the target cell. For example and without limitation, the target cell may be a T cell, B cell, dendritic cell, NK cell, macrophage, platelet, erythrocyte, epithelial cell, endothelial cell, neutrophil, cancer cell, senescent cell, or stem cell. For example and without limitation, the target may be 5T4, ALDH1, alpha V beta 6 integrin, ARMX3, AXL, B2MG, BCMA, C4.4A, CA6, CA9, Cadherin 6, CAIX, carcinoembryonic antigen (CEA), CCR1, CCR10, CCR4, CCR5, CCR6, CCR8, CD1d, CD3, CD4, CD5, CD8, CD9, CD11c, CD13, CD14, CD15, CD16, CD16A, CD19, CD20, CD22, CD25, CD27, CD28, CD30, CD31, CD32, CD32B, CD33, CD34, CD37, CD38, CD39, CD41, CD44, CD44v6, CD45R, CD45RA, CD45RO, CD47, CD49b, CD51, CD54, CD56, CD57, CD61, CD62, CD62E, CD62L, CD64, CD66b, CD69, CD70, CD74, CD79B, CD79 alpha/beta, CD80, CD81, CD83, CD86, CD94/NKG2, CD103, CD117, CD119, CD123, CD127, CD133, CD134, CD137, CD138, CD146, CD154, CD160, CD161/NK1.1, CD164, CD171, CD172a, CD180, CD194, CD197, CD202b, CD205, CD206, CD207, CD215, CD223, CD235a, CD252, CD268, CD269, CD272, CD273, CD282, CD284, CD307d, CD309, CD317, CD326, CD369, CD370, c-Kit, c-MET, Criptoprotein, Crth2, CTLA-R, CXCR3, CXCR4, CXCR5, DCIR2, DEP1, DLL3, EBP50, EDG-1/S1P1, EDNRB, EFNA4, EGFR, EGFRvIII, EMR1, ENPP3, epithelial cell adhesion molecule (EpCAM), EphA2, ErbB, ErbB2, FAP, Fas ligand, FGFR2, FGFR3, fibroblast activation protein (FAP), FLT3, folate receptor-alpha, GARP, GD2, GITR, glypican 3, gp100, gpA33, GPC3, GPNMB, GUCY2C, HGF, HER2, HERS, HLA-DR, IFN-gamma R, IgG, IGF-1R, IL-1R5, IL-1 RI, IL-6R, IL-6R alpha, IL-13 receptor α, IL-18R alpha, IL-21R, IL-23R, kappa light chain, KIR Family, L1 cell adhesion molecule (L1CAM), LAMP-1, LANCL1, LAP, Lewis Y, LFA-1, LIV-1, LRRC15, MAGE family members, mesothelin, MET, MHCII, MSLN, MUC1, MUC16, NaPi2b, Nectin-4, NKG2D, NOTCH3, NTAL, NY-ESO-1, p-CAD, PD-1, PDGFR, PLD3, prostate specific cancer antigen (PSCA), prostate-specific membrane antigen (PSMA), PTK7, RORI, S1, Siglec-H, SLC44A4, SLITRK6, STEAP1, STX4, TCR alpha/beta, TF, TGFB RII, TGM2, TIM-1, TLR1, TLR2, TLR6, TLR7, TLR10, TNFSF7, TROP-2, VAMPS, VEGFR, VEGF-R2, vimentin, or VPS26A.

The inclusion of two different binding moieties makes the nucleic acid nanoparticle bivalent. Consequently, the nanoparticle binds to two different types of cells simultaneously and brings them into proximity to facilitate interactions between them. For example, one target cell may be a tumor cell or an infected cell, and the other cell may be an immune cell. The immune cell may be any of the immune cells described above. Preferably, the immune cell is a T cell, NK cell, NKT cell, or macrophage. By promoting association between the immune cell and the tumor cell or infected, the composition abets killing of the tumor cell or infected cell by the immune cell. A similar approach using bispecific antibodies has been described in, for example, Fan et al., Bispecific antibodies and their applications, J. Hematology and Oncology, 8:130 (2015), DOI 10.1186/s13045-015-0227-0, the contents of which are incorporated herein by reference.

The nanoparticle may contain multiple binding moieties that all bind different targets. For example, the nanoparticle may contain 3, 4, 5, or more binding moieties. Two or more of the targets may be on the same target cell. Binding of multiple targets on the same target cell increases the avidity of binding of the nanoparticle to the target cell and increases the likelihood that the nanoparticle will bind and remain bound to the target cell.

In other aspects, the invention provides compositions having moieties that bind multiple targets on the same cell to alter the activity of multiple pathways within the cell.

Figure 7:
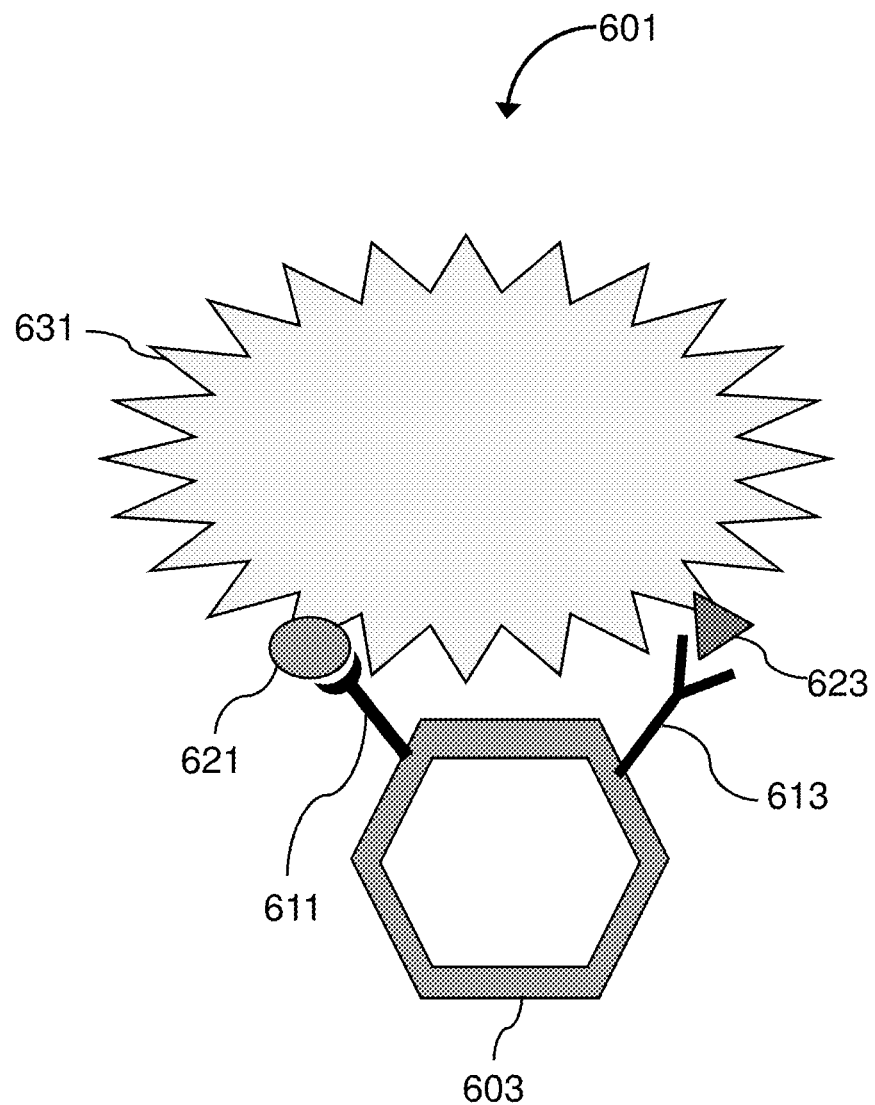
FIG. 7 illustrates a composition according to an embodiment of the invention.

FIG. 7 illustrates a composition 601 according to an embodiment of the invention. The composition 601 includes a nucleic acid nanoparticle 603 linked to a binding moiety 611 that binds to a target 621 on a target cell 631. The nucleic acid nanoparticle 603 is also linked to another binding moiety 613 that binds to another target 623 on the same target cell 631. Binding of one target moiety 611 to its target 621 alters the activity of one pathway in the target cell 631, and binding of the other target moiety 613 to its target 623 alters the activity of another pathway in the target cell 631. The nucleic acid nanoparticle 603 may be linked to additional binding moieties that bind to additional targets. The additional targets may be located on the target cell 631 or elsewhere.

The targets 621 and 623 may be receptors on the surface of the target cell 631. Myriad cell surface receptors that affect intracellular signaling pathways are known in the art, and many fall within a particular class. For example and without limitation, each target may independently be a ligand-gated ion channel receptor, enzyme-coupled receptor, G-protein-coupled receptor. Sub-classed of enzyme-coupled receptors include receptor tyrosine kinases, tyrosine kinase associated receptors, receptor-like tyrosine phosphatases, receptor serine/threonine kinases, receptor guanylyl cyclases, or histidine kinase associated receptors. A target may be EGFR, HER2, HER3, or IGF-1R.

Binding of the targets 621 and 623 may alter the activity of any type of pathway. For example and without limitation, binding may alter the activity of a signaling, biochemical, metabolic, or genetic pathway. Binding may increase or decrease the activity of the pathway. Preferably, the different pathways are involved in a common disease or disorder. For example, aberrant activity in each pathway may be associated with the disease or disorder, such as cancer. A similar approach using bispecific antibodies to block two pathways simultaneously using bispecific antibodies has been described in, for example, Fan et al., Bispecific antibodies and their applications, J. Hematology and Oncology, 8:130 (2015), DOI 10.1186/s13045-015-0227-0, the contents of which are incorporated herein by reference.

In other aspects, the invention provides compositions having moieties that bind multiple cell-free circulating effectors.

Figure 8:
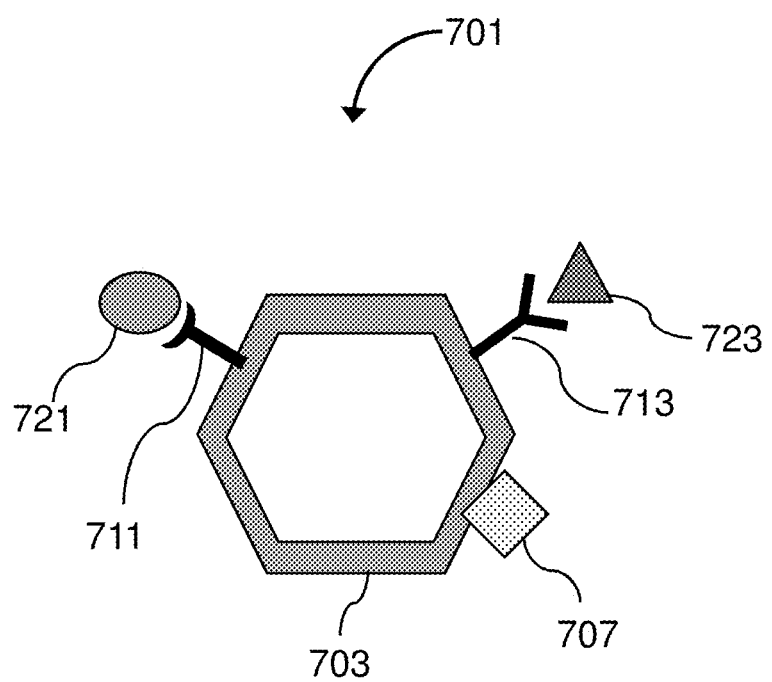
FIG. 8 illustrates a composition according to an embodiment of the invention.

FIG. 8 illustrates a composition 701 according to an embodiment of the invention. The composition 701 includes a nucleic acid nanoparticle 703 linked to a binding moiety 711 that binds to a cell-free circulating effector 721. The nucleic acid nanoparticle 703 is also linked to another binding moiety 713 that binds to another cell-free circulating effector 723. The nucleic acid nanoparticle 703 may also be linked to a targeting moiety 707. The targeting moiety 707 may bind to a target on or in a target cell that is responsive to the cell-free circulating effectors 721 and 723.

Cell Free Circulating Effectors

The cell-free circulating effectors 721 and 723 may be any extracellular component that exerts an effect on a target cell. For example and without limitation, a cell-free circulating effector may be a growth factor, hormone, cytokine, pathogen, virus, microbe, mutagen, or carcinogen. For example and without limitation, a cell-free circulating effector may be Ang-2, DLL4, IL-13, IL-17A, IL-17F, IL-2, IL-4, TNF-alpha, or VEGF. The different effectors may act on the same target cell, or they may act on different target cells. The different effectors may alter the activities of different signaling pathways. The different signaling pathways may be involved in a common disease or disorder. For example, aberrant activity in each pathway may be associated with the disease or disorder, such as cancer. A similar approach using bispecific antibodies to bind to multiple circulating effectors has been described in, for example, Kienast et al, Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy, Clin Cancer Res. 19(24):6730-40 (2013), doi: 10.1158/1078-0432.CCR-13-0081; and Fan et al., Bispecific antibodies and their applications, J. Hematology and Oncology, 8:130 (2015).

Formulations

The invention also provides pharmaceutical compositions containing any of the compositions described above. The composition may be formulated for a particular route of administration. For example, the composition may be formulated for oral, intravenous, enteral, parenteral, dermal, buccal, topical (including transdermal), injection, intravenous, nasal, or pulmonary administration. The composition may be formulated for administration with or on an implantable medical device (e.g., stent or drug-eluting stent or balloon equivalents). Preferably, the composition is formulated for oral or intravenous administration.

A pharmaceutical composition may be in a form suitable for oral use, for example, as tablets, troches, lozenges, fast-melts, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the compounds in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452; and U.S. Pat. No. 4,265,874, to form osmotic therapeutic tablets for control release. Preparation and administration of compounds is discussed in U.S. Pat. No. 6,214,841; and U.S. Pub. 2003/0232877, the contents of which are incorporated by reference herein in their entirety.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compositions in a vegetable oil, for example, *Arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or *Arachis* oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, and agents for flavoring and/or coloring.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

The compositions of the method may be prepared by inkjet printing, such as continuous inkjet (CIJ) printing or drop-on-demand (DoD) printing. DoD printing technology is capable of dispensing predictable, and highly controllable, dosage droplets onto edible substrates for consumption. By changing the drop size and formulation, the dosage can be specifically tuned to a patient's needs. DoD printing may be integrated with synthesis of one or more components of the composition. The component may be deposited onto the substrate first. Liquid excipients may then be added in sequential layers. Droplet generators are described in, for example, Jakiela et al. (Micromachines 2014, 5, 1002-1011); Andrukh et al. (Langmuir, 2011, 27 (6), pp 3206-3210); and Fan et al., (Sensors and Actuators A: Physical; Volume 147, Issue 2, 3 Oct. 2008, Pages 649-655); Icten et al., (Journal of pharmaceutical sciences 104.5 (2015):1641-1649); and Alomari et al. (International Journal of Pharmaceutics 494.2 (2014): 568-577), the contents of each of which are incorporated herein by reference.

Substrates may be an administrable carrier on which the nucleic acid nanoparticle or other composition is printed. For oral administration it is important that the substrate can be ingested. While the ability to jet many drugs has been demonstrated, some studies do not deposit the active onto substrates fit for human consumption. The use of a range of different substrates, including edible substrates such as icing sheets, polymeric and starch films and nonedible substrates, such as paper and acetate, has been reported. For example and without limitation, the substrate may be a hydroxypropyl methyl cellulose (HPMC) film, edible icing sheet, uncoated paper, coated paper, and polyethylene terephthalate (PET) film, glass cover slip coated in flutec fluid to increase hydrophobicity, orodispersible film, copy paper, water impermeable transparency film, icing sheet, PET film, HPC film, clear acetate film, starch film, uncoated wood-free paper, triple-coated inkjet paper, double-coated sheet, PTFE films over a clear transparency film, copy paper, and photocopy paper Drying helps in reducing the solvent content and enhances the uniformity of printed doses. In traditional printing on paper, absorptive drying is the main mechanism at ambient conditions as the liquid penetrates the fiber network of the papers. Evaporative drying could also be employed to further shorten the drying time using hot air convection, keeping temperatures below 50° C. for sensitive materials. It would also be possible to heat the substrate itself. It is important to investigate the effect of drying on the physical state of the active, if any, and its effect on the therapeutic outcome of the drug Methods The invention also provides methods of treating a disease, disorder, or condition in a subject by providing a composition of the invention. Providing may include administration of the compound. For example, the composition may be administered orally, intravenously, enterally, parenterally, dermally, buccally, topically (including transdermally), by injection, intravenously, nasally, pulmonarily, or with or on an implantable medical device (e.g., stent or drug-eluting stent or balloon equivalents). Providing may also include selling, distributing, procuring, or otherwise physically proffering the composition.

The disease, disorder, or condition may be any malady that can be ameliorated by a composition of the invention. Preferably, the disease, disorder, or condition is cancer or an infection.

The invention also provides methods of using the compositions for agricultural purposes. For example, the compositions may be used to treat diseases or infections in plants, such as crops, or non-human animals, such as livestock animals.

EXAMPLES

Example 1

Nanoparticles having various structural configurations and stoichiometries were generated RNA monomers, aptamers, and mRNAs.

Figure 9:
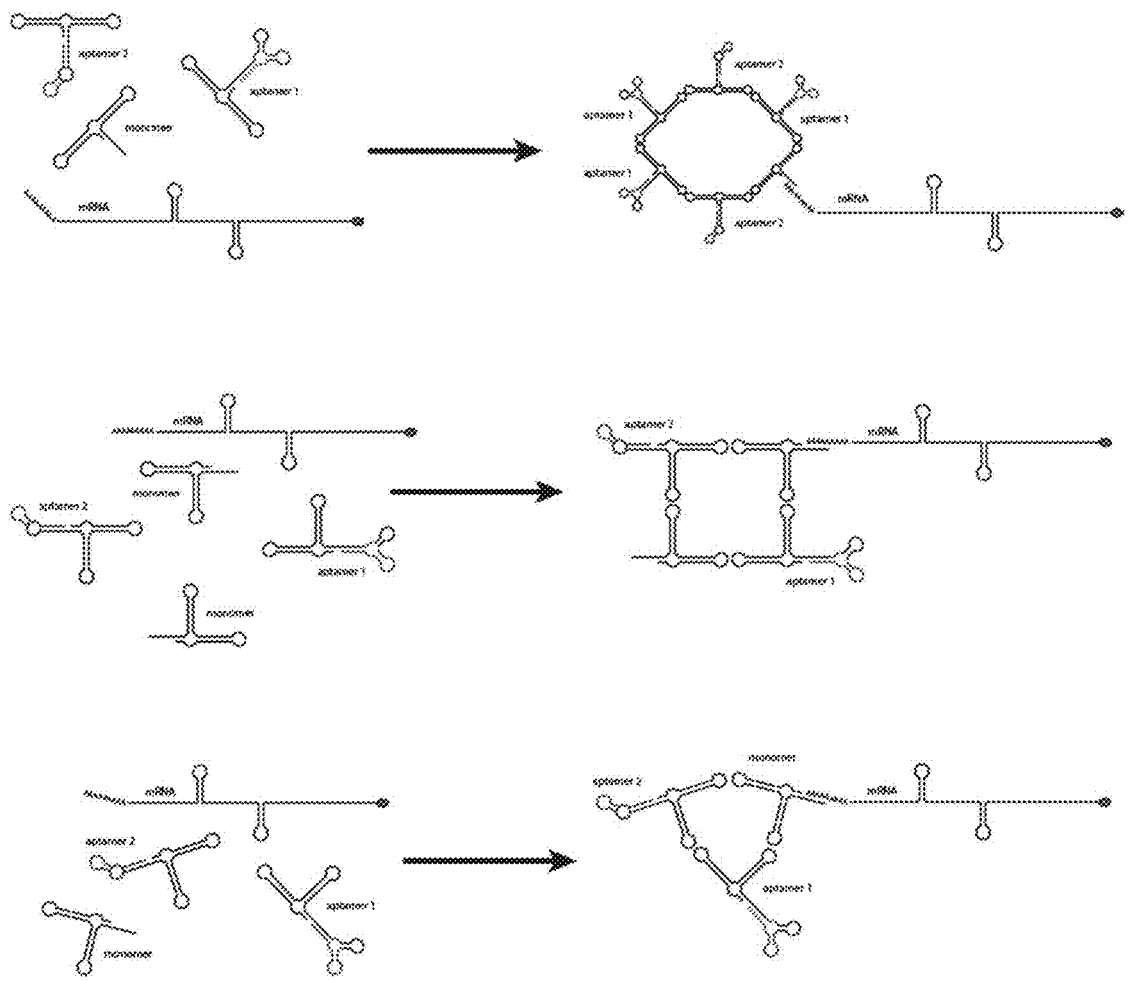
FIG. 9 is a diagram showing assembly of RNA nanoparticles of the invention.

FIG. 9 is a diagram showing assembly of RNA nanoparticles of the invention. The starting components include aptamer 1, aptamer 2, RNA monomer, and mRNA. The top row shows assembly of a hexameric particle having a stoichiometric ratio of aptamer 1 to aptamer 2 to mRNA of 3:2:1. The middle row shows assembly of a tetramer particle having a stoichiometric ratio of aptamer 1 to aptamer 2 to mRNA of 1:1:1. The bottom row shows assembly of a trimer particle having a stoichiometric ratio of aptamer 1 to aptamer 2 to mRNA of 1:1:1. Assembled RNA nanoparticles have poly-U tails that are complementary to poly-A tails in mRNA, thereby allowing attachment of mRNA to the nanoparticle.

Example 2

Table 1 provides the sequences of exemplary RNA monomers used to form RNA nanoparticles and the functionality of each RNA monomer.

TABLE 1

| Name | Functionality | Sequence | SEQ ID NO. |
|---|---|---|---|
| Trimer components | | | |
| tr3a_mR3u20 | trimer 3, monomer a, for mRNA 3 with u20 | GGCAACCGCACAGACUCUGUGAAGGAGGCACGCAGAGUCUGUGCCCAAAUCAACAAG AGGUGAAGCCUGCACGCCUCUUGUUGAUGGUUGCCAUUUUUUUUUUUUUUUUUUUU | 1 |
| tr3b_mR3u20 | trimer 3, monomer b, for mRNA 3 with u20 | GGCAACCGCACAGACUCUGUGAAGCGAGCACGCAGAGUCUGUGCCCAAAUCAACAAG AGGUGAAGCCUCCACGCCUCUUGUUGAUGGUUGCCAUUUUUUUUUUUUUUUUUUUU | 2 |

TABLE 1-continued

| Name | Functionality | Sequence | SEQ ID NO. |
|---|---|---|---|
| tr3c_mR3u20 | trimer 3, monomer c, for mRNA 3 with u20 | GGCAACCGCACAGACUCUGUGAAGCAGGCACGCAGAGUCUGUGCCCAAAUCAACAAG AGGUGAAGCUCGCACGCCUCUUGUUGAUGGUUGCCAUUUUUUUUUUUUUUUUUU | 3 |
| tr3a_a1_Gint4T | trimer 3, monomer a, for aptamers Gint4.T, anti-PDGFRβ | GGCAACCGCACAGACUCUGUGAAGGAGGCACGCAGAGUCUGUGCCCAAAUCAACAAG AGGUGAAGCCUGCACGCCUCUUGUUGAUGGUUGCCgUGUCGUGGGGCAUCGAGUAA AUGCAAUUCGACAc | 4 |
| tr3a_a1_CL4 | trimer 3, monomer a, for aptamers CL4, anti-EGFR/EGFRvIII | GGCAACCGCACAGACUCUGUGAAGGAGGCACGCAGAGUCUGUGCCCAAAUCAACAAG AGGUGAAGCCUGCACGCCUCUUGUUGAUGGUUGCCgGCCUUAGUAACGUGCUUUGAU GUCGAUUCGACAGGAGGCc | 5 |
| Tetramer components | | | |
| tt3a_mR3u20 | tetramer 3, monomer a, for mRNA 3 with u20 | GGGACGGACGCGAAUCUAGUCUAAGGAGGCAAGACUAGAUUCGCCCUGAAGAGUAGC GAAGUGGACACGCUACUCUUCAGGUAACGUUCCUCAUUUUUUUUUUUUUUUUUUUU | 6 |
| tt3b_mR3u20 | tetramer 3, monomer b, for mRNA 3 with u20 | GGGACGGACGCGAAUCUAGUCUAAGUCCACAAGACUAGAUUCGCCCUGAAGAGUAGC GAAGCCUGCACGCUACUCUUCAGGUAACGUUCCUCAUUUUUUUUUUUUUUUUUUUU | 7 |
| tt3c_mR3u20 | tetramer 3, monomer c, for mRNA 3 with u20 | GGGACGGACGCGAAUCUAGUCUAAGGAGGCAAGACUAGAUUCGCCCUGAAGAGUAGC GAAGCCACGCUACUCUUCAGGUAACGUUCCUCAUUUUUUUUUUUUUUUUUUUU | 8 |
| tt3d_mR3u20 | tetramer 3, monomer d, for mRNA 3 with u20 | GGGACGGACGCGAAUCUAGUCUAAGCUCGCAAGACUAGAUUCGCCCUGAAGAGUAGC GAAGCCUCCACGCUACUCUUCAGGUAACGUUCCUCAUUUUUUUUUUUUUUUUUUUU | 9 |
| tr3a_a1_CL4 | trimer 3, monomer a, for aptamers CL4, anti-EGFR/EGFRvIII | GGCAACCGCACAGACUCUGUGAAGGAGGCACGCAGAGUCUGUGCCCAAAUCAACAAG AGGUGAAGCCUGCACGCCUCUUGUUGAUGGUUGCCgGCCUUAGUAACGUGCUUUGA UGUCGAUUCGACAGGAGGCc | 5 |
| tt3a_a1_Gint4T | tetramer 3, monomer a, for aptamers Gint4.T, anti-PDGFRβ | GGGACGGACGCGAAUCUAGUCUAAGGAGGCAAGACUAGAUUCGCCCUGAAGAGUAGC GAAGUGGACACGCUACUCUUCAGGUAACGUUCCgUGUCGUGGGGCAUCGAGUAAAU GCAAUUCGACAc | 10 |
| tt3a_a1_CL4 | tetramer 3, monomer a, for aptamers CL4, anti-EGFR/EGFRvIII | GGGACGGACGCGAAUCUAGUCUAAGGAGGCAAGACUAGAUUCGCCCUGAAGAGUAGC GAAGUGGACACGCUACUCUUCAGGUAACGUUCCgGCCUUAGUAACGUGCUUUGAUG UCGAUUCGACAGGAGGCc | 11 |
| Hexamer components | | | |
| h3a_mR3u20 | hexamer 3, monomer a, for mRNA 3 with u20 | GGGAACGGUCCACUCGUUCCCGUCACUAGAACCAUCCUAGUGACCAUUUUUUUUUUU UUUUUUUU | 12 |
| h3b_mR3u20 | hexamer 3, monomer b, for mRNA 3 with u20 | GGGAACGGGUGACUCGUUCCCGUCACUAGAGUGGACCUAGUGACCAUUUUUUUUUUU UUUUUUUU | 13 |
| h3c_mR3u20 | hexamer 3, monomer c, for mRNA 3 with u20 | GGGAACGACCACGACGUUCCCGUCACUAGAGUCACCCUAGUGACCAUUUUUUUUUUU UUUUUUUU | 14 |
| h3d_mR3u20 | hexamer 3, monomer d, for mRNA 3 with u20 | GGGAACGGCGAAGUCGUUCCCGUCACUAGUCGUGGUCUAGUGACCAUUUUUUUUUUU UUUUUUUU | 15 |
| h3e_mR3u20 | hexamer 3, monomer e, for mRNA 3 with u20 | GGGAACGGAGACGUCGUUCCCGUCACUAGACUUCGCCUAGUGACCAUUUUUUUUUUU UUUUUUUU | 16 |
| h3f_mR3u20 | hexamer 3, monomer f, for mRNA 3 with u20 | GGGAACGGAUGGUUCGUUCCCGUCACUAGACGUCUCCUAGUGACCAUUUUUUUUUUU UUUUUUUU | 17 |
| h3a_a1_Gint4T | hexamer 3, monomer a, for aptamers Gint4.T | GGGAACGGUCCACUCGUUCCCGUCACUAGAACCAUCCUAGUGACCAcUGUCGUGGGG CAUCGAGUAAAUGCAAUUCGACAG | 18 |

Example 3

The effect of 2'F pyrimidines on self-assembly of trimeric nanoparticles was analyzed. Samples were prepared in final molar amount of 20 pmoles of monomer/multimer per experiment. Each sample was diluted in water, mixed and associated by the following the protocol: incubation at 90° C. for 3 minutes; cool to 4° C. and add 1 mM $Mg^{2+}$ in TB; ramping incubation 55-20° C. for 30 minutes; cool to 4° C.; and analyze by native 10% polyacrylamide gel electrophoresis (PAGE) at 300V for 4 hours.

Figure 10:
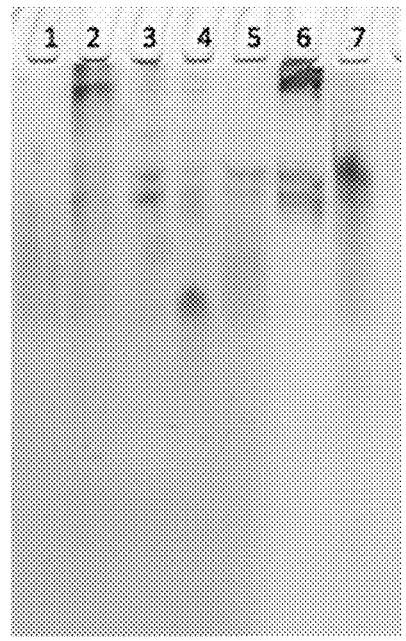
FIG. 10 is an image of a stained gel following native PAGE analysis of RNA components of a nanoparticle of the invention.

FIG. 10 is an image of a stained gel following native PAGE analysis of RNA components. Samples are as follows: lane 1, monomer 1GA (normal); lane 2, Trimer 1G: A+B+C (normal); lane 3, monomer 2'F1GA; lane 4, monomer 2'F1GB; lane 5, monomer 2'F1GC; lane 6, trimer 2'F1G: A+B+C; and lane 7, dimer 1G: A+B (dimer).

Example 4

The effect of 2'F pyrimidines on serum stability of trimers containing 2'F pyrimidines was analyzed. Samples containing 20 pmoles of monomers were prepared in 20 μL, incubated in various conditions, and analyzed by native PAGE.

Figure 11:
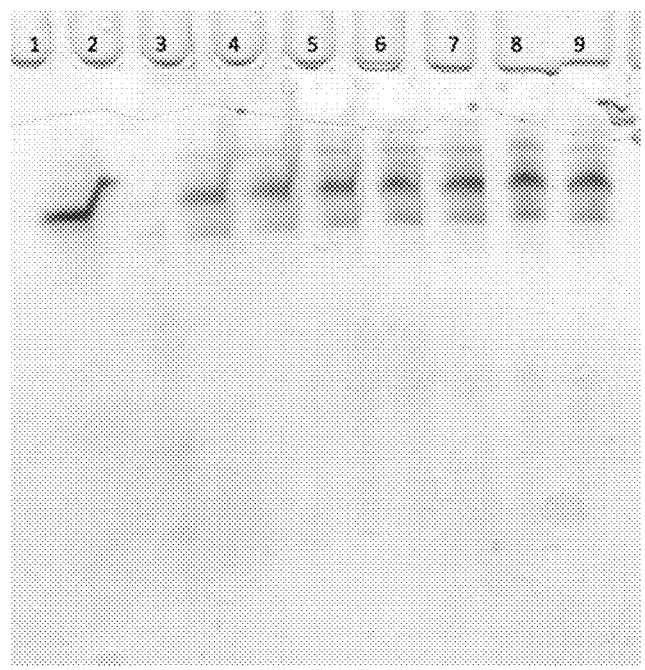
FIG. 11 is an image of a stained gel following denaturing PAGE analysis of RNA components of a nanoparticle of the invention.

FIG. 11 is an image of a stained gel following denaturing PAGE analysis of RNA components. Prior to PAGE, samples were incubated as follows: lane 1, monomer 1GA (normal) in 1×TB incubated at 37° C. for 30 minutes; lane 2, monomer 1GA (normal) in 1% FBS incubated at 37° C. for 30 minutes; lane 2, mix of 2'F monomers (A:B:C 1:1:1) in 1×TB incubated at 37° C. for 30 minutes; lane 4, mix of 2'F monomers (A:B:C 1:1:1) in 1×TB; lane 5, mix of 2'F monomers (A:B:C 1:1:1) in 1% FBS—incubated at 37° C. for 5 minutes; lane 6, mix of 2'F monomers (A:B:C 1:1:1) in 1% FBS incubated at 37° C. for 15 minutes; lane 7, mix of 2'F monomers (A:B:C 1:1:1) in 1% FBS incubated at 37° C. for 30 minutes; lane 8, mix of 2'F monomers (A:B:C 1:1:1) in 1% FBS incubated at 37° C. for 60 minutes; and lane 9, mix of 2'F monomers (A:B:C 1:1:1) in 1% FBS incubated at 37° C. for 90 minutes. After incubation, samples were supplemented with Urea/EDTA buffer and applied on the 10% denaturing PAGE and run at 300V for 4 hours.

Non-modified monomers are degraded 30 minutes after being incubated with 1% FBS.

Example 5

Efficiency of mRNA delivery using RNA nanoparticles was analyzed. A431 epidermoid carcinoma cells were seeded at 10,000 cells/well in triplicate in black 96-well plates and transfected with various delivery systems containing mRNA encoding GFP.

For Jet Messenger experiments, the following protocol was used: 50 ng mRNA, 5 µl mRNA buffer, and 0.1 µl of Jet messenger was added to each well. Transfection was performed in 50 µl of DMEM containing 10% FBS. Four hours after transfection, 100 µl DMEM containing 10% FBS was added to each well.

For Saint Red experiments, the following protocol was used: 50 ng mRNA was added to each well. Transfection was performed in 80 µl of OPTIMEM. The transfection mixture was made by separately preparing RNA in HBSS+/+ buffer and Saint Red in HBSS+/+ buffer and mixing RNA+SAINT RED at 1:1 ratio. The final transfection volume was 20 Five hours after transfection, 100 µl DMEM containing 10% FBS was added to each well to produce a final volume of 200 µl.

Fluorescence images were captured 48 hours after transfection on a 20× objective. The data was quantified using the ImageJ software by determining the Integrated Density per field of view and normalized to mRNA alone.

Figure 12:
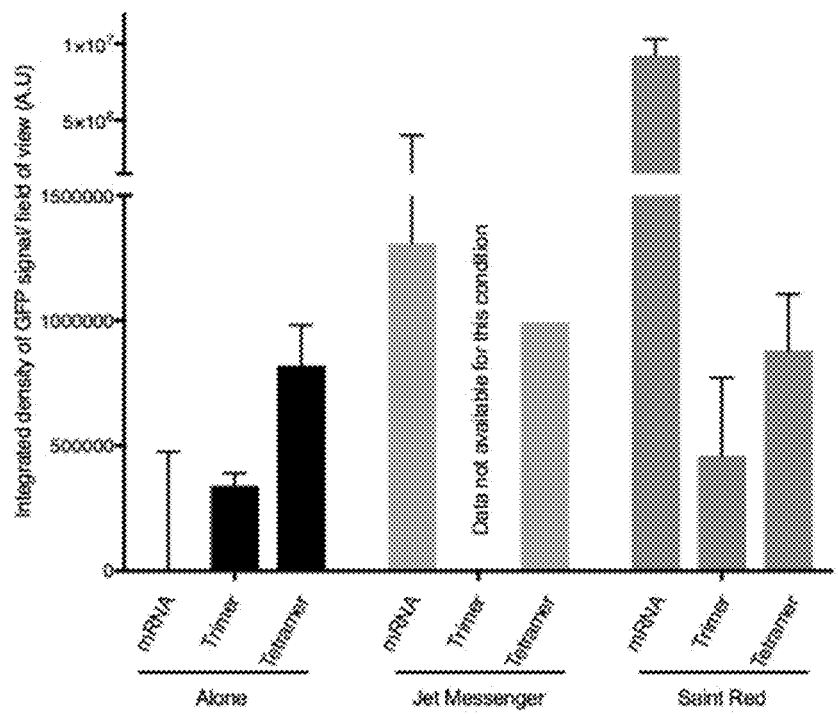
FIG. 12 is graph showing GFP signal from mRNA delivered by various vehicles.

FIG. 12 is graph showing GFP signal from mRNA delivered by various vehicles. Black bars represent samples that received only GFP mRNA, light grey bars represent samples that also received Jet Messenger, and dark grey bars represent samples that also Saint Red. As indicated on graph, cells were given mRNA not bound to nanoparticles, mRNA bound to trimers, or mRNA bound to tetramers.

Trimer and tetramer RNA structures lead to increased expression of GFP mRNA as compared to mRNA alone.

Example 6

The safety profile of the trimer-GFP mRNA construct was analyzed by measuring induction of cytotoxicity. A431 epidermoid carcinoma cells were seeded at 10,000 cells/well in triplicate in black 96-well plates and transfected with trimer-GFP mRNA constructs. 72 hours after the addition of trimers, the media was removed and 50 µL of serum-free media and 50 µL of MTT solution were added into each well, and the plate was incubated for 2 hours at 37° C. 150 µL of MTT solvent was then added into each well, and plates were incubated on an orbital shaker for 15 minutes protected from light. The absorbance at 590 nm ($OD_{590}$) was read, and the triplicate values were normalized to those wells that contained mRNA alone.

Figure 13:
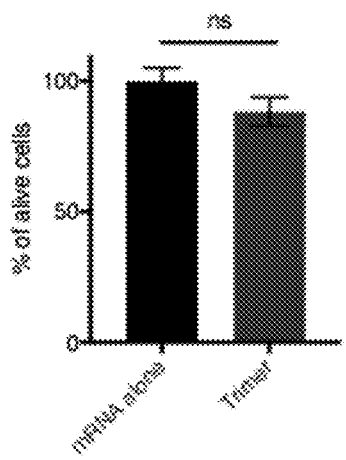
FIG. 13 is graph showing cell viability in MTT assay following transfection with mRNA alone or attached to a trimeric nanoparticle of the invention.

FIG. 13 is graph showing cell viability in MTT assay following transfection with mRNA alone or attached to a trimeric nanoparticle.

The trimer construct does not display significant cytotoxicity effects on A431 cells.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A composition comprising:
   - a RNA nanoparticle comprising at least one RNA molecule having at least two consecutive uridine residues at its 3' end; and
   - at least one nucleic acid having at least two consecutive adenosine residues at its 3' end and encoding a gene product that is expressed on a surface of a target cell, the at least one nucleic acid being linked to the RNA nanoparticle by base-pairing between the at least two consecutive uridine residues at the 3' end of the at least one RNA molecule and the at least two consecutive adenosine residues at the 3' end of the at least one nucleic acid, the at least one nucleic acid being mRNA that is different from the at least one RNA molecule.

2. The composition of claim 1, wherein the RNA nanoparticle is selected from the group consisting of a nanoarray, nanocage, nanocube, nanoprism, nanoring, nanoscaffold, and nanotube.

3. The composition of claim 2, wherein the RNA nanoparticle is a nanoring.

4. The composition of claim 3, wherein the nanoring is a hexamer.

5. The composition of claim 3, wherein the nanoring is a tetramer.

6. The composition of claim 3, wherein the nanoring is a trimer.

7. The composition of claim 1, wherein the gene product is a polypeptide or protein.

8. The composition of claim 7, wherein the polypeptide or protein is a receptor.

9. The composition of claim 8, wherein the receptor is a chimeric antigen receptor.

10. The composition of claim 1, further comprising:
    - a targeting moiety that binds to a target on a surface of the target cell, the target moiety being linked to the RNA nanoparticle.

11. The composition of claim 10, wherein the targeting moiety is selected from the group consisting of an antibody, aptamer, ligand, nucleic acid, peptide, protein, and receptor.

12. The composition of claim 11, wherein the targeting moiety is an aptamer.

13. The composition of claim 12, wherein the aptamer comprises one or more modified nucleotides.

14. The composition of claim 13, wherein the one or more modified nucleotides comprise at least one selected from the group consisting of a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholino, and phosphorothioate modification.

15. The composition of claim 10, wherein the target is selected from the group consisting of 5T4, ALDH1, alpha V beta 6 integrin, ARMX3, AXL, B2MG, BCMA, C4.4A, CA6, CA9, Cadherin 6, CAIX, carcinoembryonic antigen (CEA), CCR1, CCR10, CCR4, CCRS, CCR6, CCR8, CD1d, CD3, CD4, CDS, CD8, CD9, CD11c, CD13, CD14, CD15, CD16, CD16A, CD19, CD20, CD22, CD25, CD27, CD28, CD30, CD31, CD32, CD32B, CD33, CD34, CD37, CD38, CD39, CD41, CD44, CD44v6, CD45R, CD45RA, CD45RO, CD47, CD49b, CD51, CD54, CD56, CD57, CD61, CD62, CD62E, CD62L, CD64, CD66b, CD69, CD70, CD74, CD79B, CD79 alpha/beta, CD80, CD81, CD83, CD86, CD94/NKG2, CD103, CD117, CD119, CD123, CD127, CD133, CD134, CD137, CD138, CD146, CD154, CD160, CD161/NK1.1, CD164, CD171, CD172a, CD180, CD194, CD197, CD202b, CD205, CD206, CD207, CD215, CD223, CD235a, CD252, CD268, CD269, CD272, CD273, CD282, CD284, CD307d, CD309, CD317, CD326, CD369, CD370, c-Kit, c-MET, Criptoprotein, Crth2, CTLA-R, CXCR3, CXCR4, CXCR5, DCIR2, DEP1, DLL3, EBP50, EDG-1/S1P1, EDNRB, EFNA4, EGFR, EGFRvIII, EMR1, ENPP3, epithelial cell adhesion molecule (EpCAM), EphA2, ErbB, ErbB2, FAP, Fas ligand, FGFR2, FGFR3, fibroblast activation protein (FAP), FLT3, folate receptor-alpha, GARP, GD2, GITR, glypican 3, gp100, gpA33, GPC3, GPNMB, GUCY2C, HGF, HER2, HER3, HLA-DR, IFN-gamma R, IgG, IGF-1R, IL-1 R5, IL-1 RI, IL-6R, IL-6 R alpha, IL-13 receptor a, IL-18R alpha, IL-21 R, IL-23 R, kappa light chain, KIR Family, L1 cell adhesion molecule (L1CAM), LAMP-1, LANCL1, LAP, Lewis Y, LFA-1, LIV-1, LRRC15, MAGE family members, mesothelin, MET, MHCII, MSLN, MUC1, MUC16, NaPi2b, Nectin-4, NKG2D, NOTCH3, NTAL, NY-ESO-1, p-CAD, PD-1, PDGFR, PLD3, prostate specific cancer antigen (PSCA), prostate-specific membrane antigen (PSMA), PTK7, RORI, S1, Siglec-H, SLC44A4, SLITRK6, STEAP1, STX4, TCR alpha/beta, TF, TGFB MI, TGM2, TIM-1, TLR1, TLR2, TLR6, TLR7, TLR10, TNFSF7, TROP-2, VAMP3, VEGFR, VEGF-R2, vimentin, and VPS26A.

16. The composition of claim 1, further comprising:
a first targeting moiety that binds to a first target on a surface of the target cell, the first target moiety being linked to the RNA nanoparticle; and
a second targeting moiety that binds to a second target on a surface of the target cell, the second targeting moiety being linked to the RNA nanoparticle and being different from the first targeting moiety.

17. The composition of claim 16, wherein the first targeting moiety and the second targeting moieties are aptamers.

18. The composition of claim 1, wherein:
the at least one RNA molecule has at least three consecutive uridine residues at its 3' end;
the at least one nucleic acid has at least three consecutive adenosine residues at its 3' end; and
the at least one nucleic acid is linked to the RNA nanoparticle by base-pairing between the at least three consecutive uridine residues at the 3' end of the at least one RNA molecule and the at least three consecutive adenosine residues at the 3' end of the at least one nucleic acid.

19. The composition of claim 1, wherein:
the at least one RNA molecule has at least four consecutive uridine residues at its 3' end;
the at least one nucleic acid has at least four consecutive adenosine residues at its 3' end; and
the at least one nucleic acid is linked to the RNA nanoparticle by base-pairing between the at least four consecutive uridine residues at the 3' end of the at least one RNA molecule and the at least four consecutive adenosine residues at the 3' end of the at least one nucleic acid.

* * * * *